US008288116B2

(12) United States Patent
Chen

(10) Patent No.: US 8,288,116 B2
(45) Date of Patent: *Oct. 16, 2012

(54) METHODS AND COMPOSITIONS FOR ISOLATING METASTATIC CANCER CELLS, AND USE IN MEASURING METASTATIC POTENTIAL OF A CANCER THEREOF

(75) Inventor: Wen-Tien Chen, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/725,036

(22) Filed: Mar. 16, 2010

(65) Prior Publication Data

US 2010/0173402 A1    Jul. 8, 2010

Related U.S. Application Data

(63) Continuation of application No. 10/220,347, filed as application No. PCT/US01/26735 on Aug. 28, 2001, now Pat. No. 7,785,810.

(60) Provisional application No. 60/231,517, filed on Sep. 9, 2000.

(51) Int. Cl.
| | |
|---|---|
| *C12Q 1/00* | (2006.01) |
| *G01N 33/53* | (2006.01) |
| *G01N 33/567* | (2006.01) |
| *G01N 33/574* | (2006.01) |
| *C02F 1/00* | (2006.01) |
| *C02F 1/26* | (2006.01) |
| *C02F 1/44* | (2006.01) |
| *B01D 11/00* | (2006.01) |
| *B01D 15/08* | (2006.01) |

(52) U.S. Cl. ....... 435/7.23; 210/600; 210/633; 210/635; 210/641; 210/644; 210/645; 428/357; 428/358; 428/372; 428/373; 428/374; 435/4; 435/7.1; 435/7.21; 436/63; 436/64; 436/86; 436/174; 436/501; 436/503

(58) Field of Classification Search ............... 210/600, 210/633, 635, 641, 644, 645; 435/4, 7.1, 435/7.21, 7.23; 436/63, 64, 86, 174, 501, 436/503; 428/357, 358, 372, 373, 374

See application file for complete search history.

(56) References Cited

U.S. PATENT DOCUMENTS

| | | | |
|---|---|---|---|
| 4,734,372 A | 3/1988 | Rotman | |
| 4,829,000 A | 5/1989 | Martin et al. | |
| 5,225,353 A | 7/1993 | Bensinger et al. | |
| 5,840,514 A | 11/1998 | Livant | |
| 5,961,923 A | 10/1999 | Nova et al. | |
| 6,087,157 A | 7/2000 | Badylak et al. | |
| 6,146,824 A | 11/2000 | Bar-Shavit | |
| 6,379,703 B1 | 4/2002 | Lyons et al. | |
| 6,379,709 B1 | 4/2002 | Slim et al. | |
| 6,428,579 B1 * | 8/2002 | Valentini | 623/23.76 |
| 6,559,119 B1 | 5/2003 | Burgess et al. | |
| 7,232,653 B1 | 6/2007 | Austrup et al. | |

FOREIGN PATENT DOCUMENTS

| | | |
|---|---|---|
| WO | EP0277837 A | 8/1988 |
| WO | WO9115245 A1 | 10/1991 |

OTHER PUBLICATIONS

Montcourrier et al., "Cathepsin D in Breast Cancer Cells Can Digest Extracellular Matrix in Large Acidic Vesicles", Cancer Research: 56, 6045-6054 (1990).

Goldstein, L.A., et al., "Identification of an alternatively spliced seprase mRNA that encodes a novel intracellular isoform", J. Biol. Chem 2000, 275:2554-2559.

Brugger, W., et al., "Approaches to dendritic cell-based immunotherapy after peripheral blood stem cell transplantation", Ann. N.Y. Acad. Sci. 1999, 872:363-371.

Mueller, S.C., et al., "A novel protease-docking function of integrin at invadopodia", J. Biol. Chem. 1999, 274:24947-24952.

Sabile, A., et al., "Efficiency of Ber-EP4 antibody for isolating circulating epithelial tumor cells before RT-PCR detection", Am. J. Clin. Pathol. 1999, 112:171-178.

Suarez-Quian, C.A., et al., "Laser capture microdissection of single cells from complex tissues", Biotechniques 1999, 26:328-335.

Baran, J., et al., "Detection of cancer cells in the blood by FACS sorting of CD45-cells", Int. J. Mol. Med. 1998, 1:573-578.

Beltinger, C.P., et al., "A simple combined microdissection and aspiration device for the rapid procurement of single cells from clinical peripheral blood smears", Mol. Pathol. 1998, 51:233-236.

Bermpohl, F., et al., "Rat dipeptidyl peptidase IV (DPP IV) exhibits endopeptidase activity with specificity for denatured fibrillar collagens", FEBS Lett. 1998, 428:152-156.

(Continued)

*Primary Examiner* — Alana Harris Dent
(74) *Attorney, Agent, or Firm* — Hoffmann & Baron, LLP

(57) ABSTRACT

The present invention relates to novel methods and compositions for detection and isolation of cancer cells with metastatic potential. The invention further relates to assays for measuring the metastatic potential of such cancer cells and drug screening assays for the identification of agents having anti-metastatic potential. The present invention further provides methods and compositions for inhibiting the metastatic potential of cancer cells by modulating the activity of serine integral membrane proteases [(SIMP) consisting of seprase and dipetidyl peptidase IV (DPPIV)] expressed on the surface of metastasizing cancer cells.

18 Claims, 29 Drawing Sheets

OTHER PUBLICATIONS

Figure 1A:
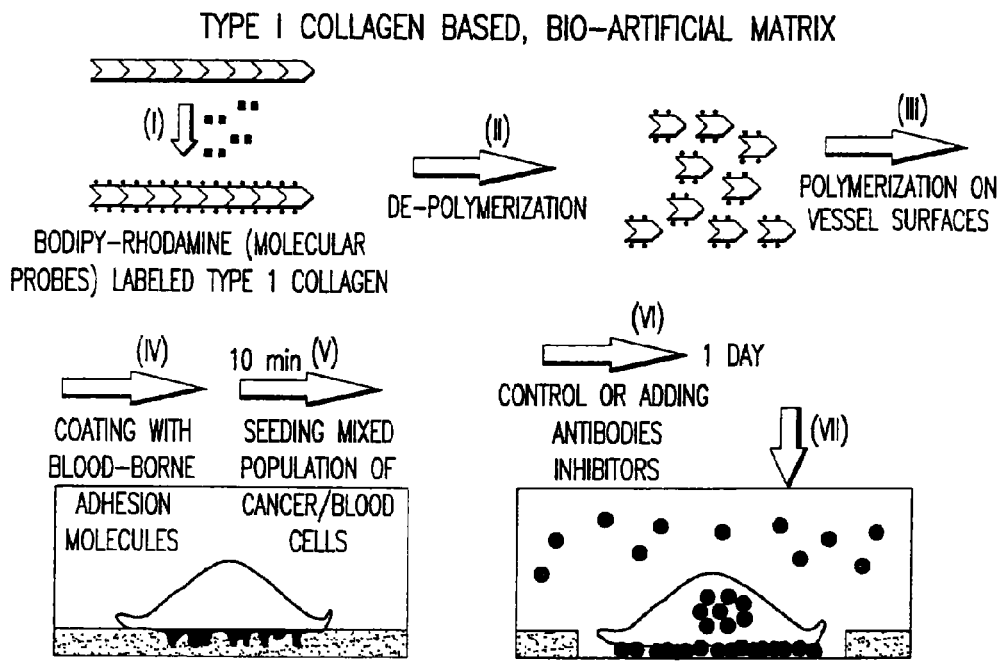

Chambers, A.F., et al., "Preclinical assessment of anti-cancer therapeutic strategies using in vivo videomicroscopy", Cancer and Metastasis Review 1998, 17:263-269.

Cheng, H.C., et al., "Lung endothelial dipeptidyl peptidase IV promotes adhesion and metastasis of rat breast cancer cells via tumor cell surface-associated fibronectin", J. Biol. Chem. 1998, 273:24207-24215.

Kelly, T., et al., "Seprase, a membrane-bound protease, is overexpressed by invasive ductal carcinoma cells of human breast cancers", Mod. Pathol. 1998, 11:855-863.

Racila, E., et al., "Detection and characterization of carcinoma cells in the blood", Proc Natl Acad Sci USA 1998, 95:4589-4594.

Denis, M.G., et al., "Detection of disseminated tumor cells in peripheral blood of colorectal cancer patients", Int. J. Cancer 1997, 74:540-544.

Goldstein, L.A., et al., "Molecular cloning of seprase: a serine integral membrane protease from human melanoma", Biochim Biophys Acta 1997, 1361:11-19.

Pineiro-Sanchez, M.L., et al., "Identification of the 170-kDa melanoma membrane-bound gelatinase (seprase) as a serine integral membrane protease", J. Biol. Chem. 1997, 272:7595-7601.

Chen, W.T., et al., "Proteases associated with invadopodia, and their role in degradation of extracellular matrix", Enzyme Protein 1996, 49:59-71.

Campana, D., et al., "Detection of minimal residual disease in acute leukemia: methodologic advances and clinical significance", Blood 1995, 85:1416-1434.

Cannistra, S.A., et al., "Expression and function of β1 and αvβ3 integrins in ovarian cancer", Gynecologic Oncology 1995, 58:216-225.

Löster, K., et al., "The cysteine-rich region of dipeptidyl peptidase IV (CD 26) is the collagen-binding site", Biochem Biophys Res Commun 1995, 217:341-348.

Brugger, W., et al., "Mobilization of tumor cells and hematopoietic progenitor cells into peripheral blood of patients with solid tumors", Blood 1994, 83:636-640.

Chen, W.T., et al., "An in vitro cell invasion assay: determination of cell surface proteolytic activity that degrades extracellular matrix", Tissue Culture Methods 1994, 16:177-181.

Morimoto, C., et al., "A key costimulatory molecule on CD4 memory T cells", Immunologist 1994, 2:4-7.

Monsky, W.L., et al., "A potential marker protease of invasiveness, seprase, is localized on invadopodia of human malignant melanoma cells", Cancer Res. 1994, 54:5702-5710.

Rill, D.R., et al., "Direct demonstration that autologous bone marrow transplantation for solid tumors can return a multiplicity of tumorigenic cells", Blood 1994, 84:380-383.

Scanlan, M.J., et al., "Molecular cloning of fibroblast activation protein alpha, a member of the serine protease family selectively expressed in stromal fibroblasts of epithelial cancers", Proc Natl Acad Sci USA 1994, 91:5657-5661.

Gulati, S.C., et al., "Rationale for purging in autologous stem cell transplantation", J Hematother 1993, 2:467-471.

Johnson, R.C., et al., "Lung endothelial dipeptidyl peptidase IV is an adhesion molecule for lung-metastatic rat breast and prostate carcinoma cells", J Cell Biol 1993, 121:1423-1432.

Songyang, Z., et al., "SH2 domains recognize specific phosphopeptide sequences", Cell 1993, 72:767-778.

Yaron, A., et al., "Proline-dependent structural and biological properties of peptides and proteins", Crit Rev Biochem Mol Biol 1993, 28:31-81.

Houghten, R.A., et al., "Generation and use of synthetic peptide combinatorial libraries for basic research and drug discovery", Nature 1991, 354:84-86.

Lam, K.S., et al., "A new type of synthetic peptide library for identifying ligand-binding activity", Nature 1991, 354:82-84.

Liotta, L.A., et al., "Cancer metastasis and angiogenesis: an imbalance of positive and negative regulation", Cell 1991, 64:327-336.

Aoyama, A., "A 170-kDa membrane-bound protease is associated with the expression of invasiveness by human malignant melanoma cells", Proc Natl Acad Sci USA 1990, 87:8296-8300.

Garin-Chesa, P., et al., "Cell surface glycoprotein of reactive stromal fibroblasts as a potential antibody target in human epithelial cancers", Proc Natl Acad Sci USA 1990, 87(18):7235-7239.P., et al., "Cell surface glycoprotein of reactive stromal fibroblasts as a potential antibody target in human epithelial cancers", Proc Natl Acad Sci USA 1990, 87 (18):7235-7239.

Chen, W.T., et al., "Proteolytic activity of specialized surface protrusions formed at rosette contact sites of transformed cells", J Exp Zool 1989, 251:167-185.

Mueller, S.C., et al., "Dynamic cytoskeleton-integrin associations induced by cell binding to immobilized fibronectin", J Cell Biol 1989, 109:3455-3464.

Piazza, G.A., et al., "Evidence for a role of dipeptidyl peptidase IV in fibronectin-mediated interactions of hepatocytes with extracellular matrix", Biochem J 1989, 262:327-334.

Bauvois, B., "A collagen-binding glycoprotein on the surface of mouse fibroblasts is identified as dipeptidyl peptidase IV", Biochem J 1988, 252:723-731.

Glaves, D., et al., "Haematogenous dissemination of cells from human renal adenocarcinomas", Br J Cancer 1988, 57:32-35.

Hanski, C., et al., "Direct evidence for the binding of rat liver DPP IV to collagen in vitro", Exp Cell Res 1988, 178:64-72.

Heins, J., et al., "Mechanism of proline-specific proteinases: (I) Substrate specificity of dipeptidyl peptidase IV from pig kidney and proline-specific endopeptidase from Flavobacterium mcningosepticum", Biochim Biophys Acta 1988, 954:161-169.

Albini, A., et al., "A rapid in vitro assay for quantitating the invasive potential of tumor cells" Cancer Res 1987, 47:3239-3245.

Chen, W.T., et al., "Local degradation of fibronectin at sites of expression of the transforming gene product pp60src", Nature 1985, 316:156-158.

Chen, W.T., et al., "Expression of transformation-associated protease(s) that degrade fibronectin at cell contact sites", J Cell Biol 1984, 98:1546-1555.

Glaves, D., "Correlation between circulating cancer cells and incidence of metastases", Br J Cancer 1983, 48:665-673.

Walter, R., et al., "Proline specific endo- and exopeptidases", Mol Cell Biochem 1980, 30:111-127.

Chen, W.T., "Induction of spreading during fibroblast movement", J Cell Biol 1979, 81:684-691.

Liotta, L.A., et al., "Quantitative relationships of intravascular tumor cells, tumor vessels, and pulmonary metastases following tumor implantation", Cancer Res 1974, 34:997-1004.

Fidler, I.T., "The relationship of embolic homogeneity, number, size and viability to the incidence of experimental metastasis", Eur J Cancer 1973, 9:223-227.

Egawa, Masayuki, "Studies on Chemosensitivity Test of Human Genitourinary Tumors Using Collagen Gel Matrix", J. Juzen Med. Soc. 1993, 102:2-9. English Abstract.

Chen, et al., "Membrane proteases as potential diagnostic and therapeutic targets for breast malignancy", Breast Cancer Research and Treatment 1994, 31(2/3):217-226.

Montcourrier et al., "Characterization of very acidic phagosomes in breast cancer cells and their association with invasion", Journal of Cell Science, 107, 2381-2391 (1994).

Terranova, V.P. et al., "Use of a reconstitute basement membrane to measure cell invasiveness and select for highly invasive tumor cells", Proc. Natl. Acad. Sci. USA, 83:465-469 (1986).

Natori, Y. et al., "Proteinuria induced by antidipeptidyl peptidase IV (GP 108); role of circulating and gluomerular antigen," Clin Exp Immuno, 95:327-332, XP001105556 (1994).

* cited by examiner

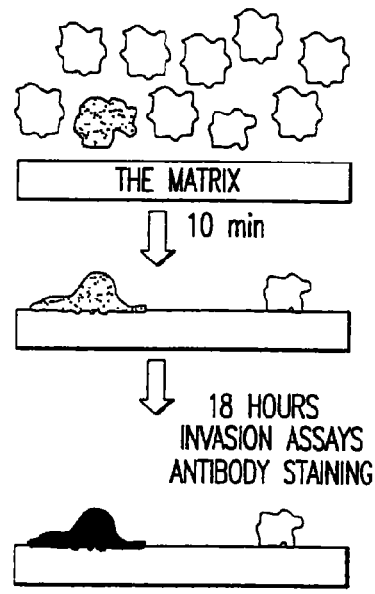

BLOOD (TISSUE) AND CANCER CELLS

"MATRIX" ISOLATION OF ADHERENT BLOOD AND CANCER CELLS

NUMERATION OF INVASIVE CANCER CELLS:
• PROGNOSTICATION,
• MONITORING THERAPEUTIC RESPONSE,
• MONITORING SURGICAL RESPONSE,
• EARLY DETECTION.

FIG. 2A

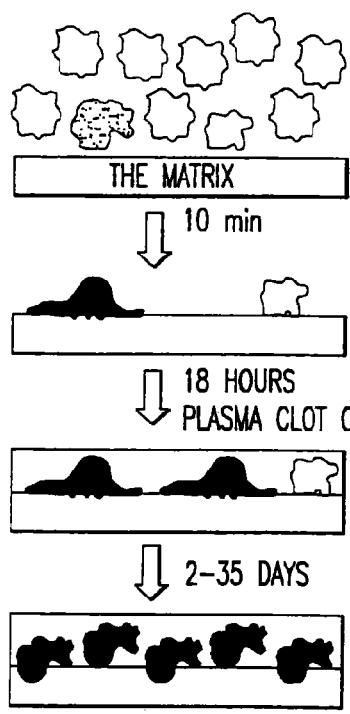

BLOOD (TISSUE) AND CANCER CELLS

REMOVAL OF ADHERENT CANCER CELLS:
• BLOOD FILTER AS A CANCER CELL TRAP

PROLIFERATION OF CANCER CELLS $>10^6$ CANCER CELLS:
• CANCER VACCINE DEVELOPMENT
• CYTOGENETIC ANALYSIS
• NEW DRUG TARGET DISCOVERY

FIG. 2B

Figures 1, 13A:
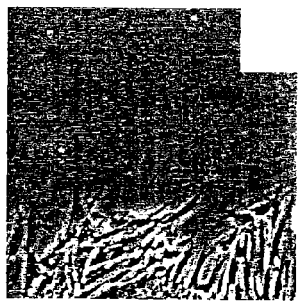
Figures 2, 13A:
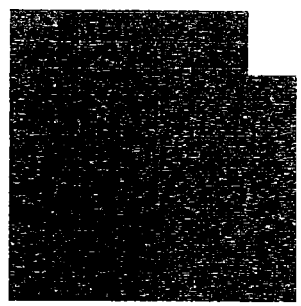
Figures 3, 13A:
Figures 4, 13A:
Figures 5, 13A:
Figures 6, 13A:
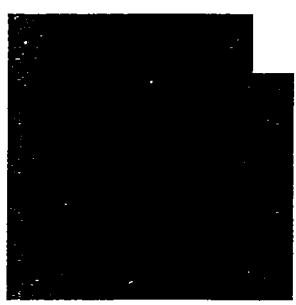

FIG.3A Hs578T 500 cells
FIG.3B Hs578T 500 cells/normal
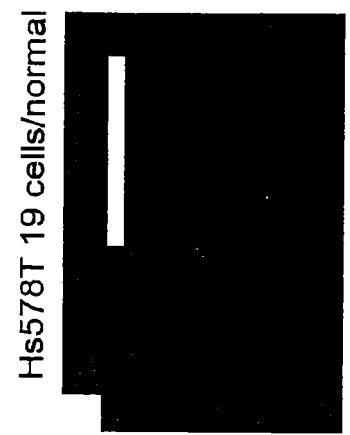
FIG.3C Hs578T 19 cells/normal
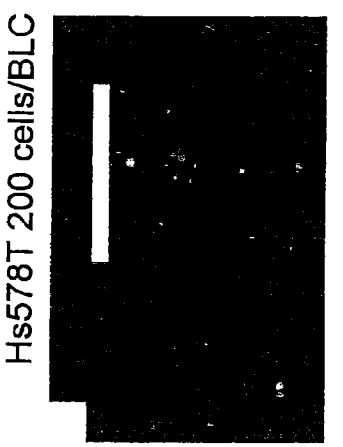
FIG.3D Hs578T 200 cells/BLC
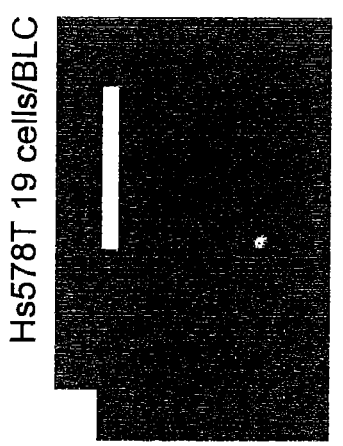
FIG.3E Hs578T 19 cells/BLC
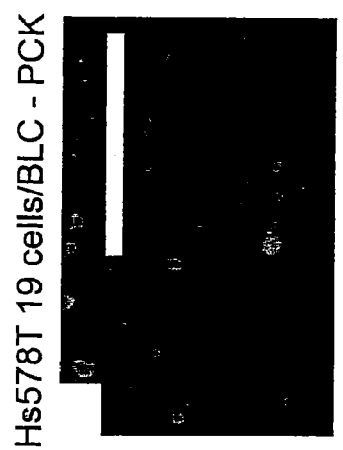
FIG.3F Hs578T 19 cells/BLC - PCK

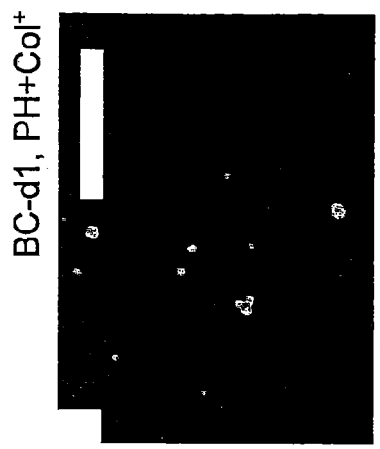
FIG. 8C — BC-d1, PH+Col⁺
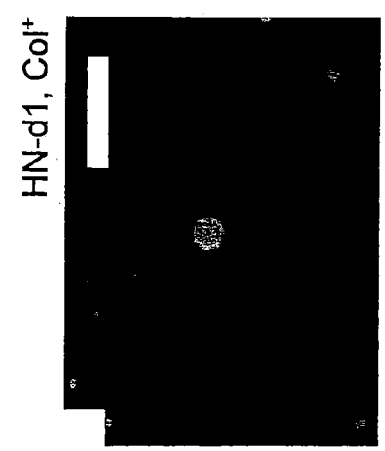
FIG. 8F — HN-d1, Col⁺
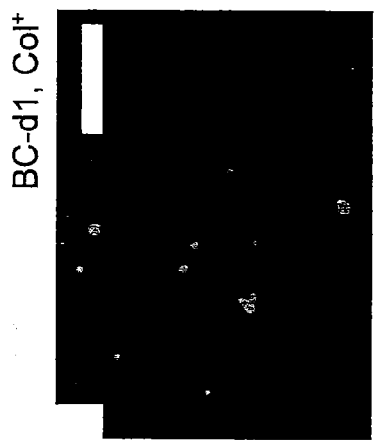
FIG. 8B — BC-d1, Col⁺
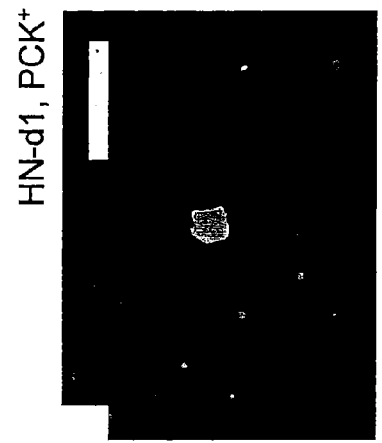
FIG. 8E — HN-d1, PCK⁺
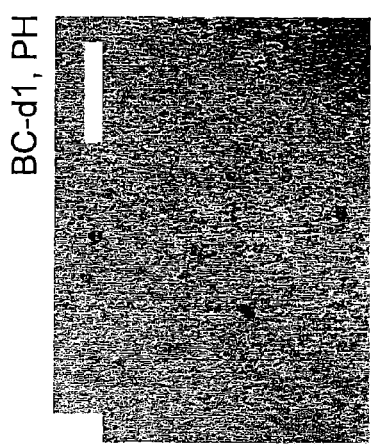
FIG. 8A — BC-d1, PH
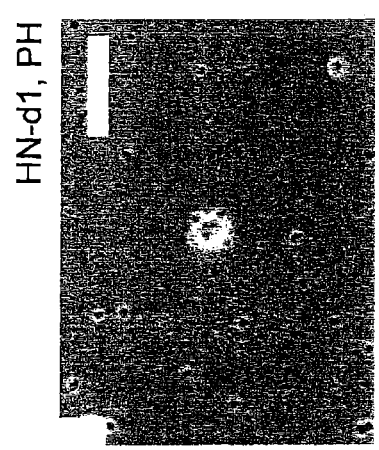
FIG. 8D — HN-d1, PH

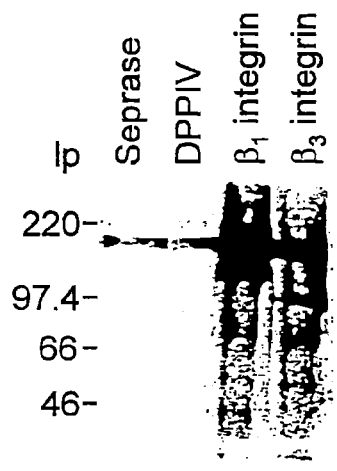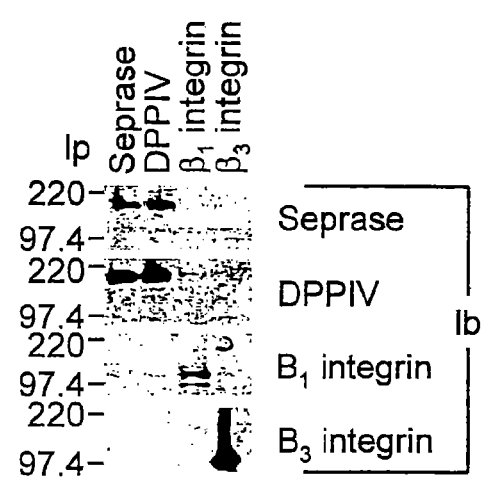
FIG.12A        FIG.12B
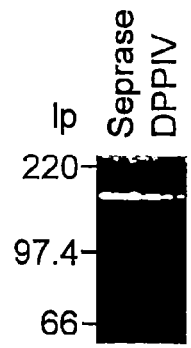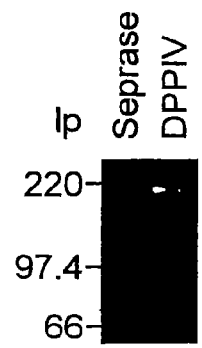
FIG.12C        FIG.12D

METHODS AND COMPOSITIONS FOR ISOLATING METASTATIC CANCER CELLS, AND USE IN MEASURING METASTATIC POTENTIAL OF A CANCER THEREOF

CROSS-REFERENCE TO RELATED APPLICATIONS

This application is a continuation of U.S. application Ser. No. 10/220,347 filed on Aug. 28, 2002, issued as U.S. Pat. No. 7,785,810 on Aug. 31, 2010, which is a U.S. National Stage Application of International PCT Application No. US01/26735 filed on Aug. 28, 2001. The specifications of U.S. application Ser. No. 10/220,347 and International PCT Application No. US01/26735 are hereby incorporated by reference in their entirety.

This application asserts priority to U.S. Provisional Application Ser. No. 60/231,517 filed on Sep. 9, 2000, the specification of which is incorporated by reference in its entirety.

This invention was made with government support under grant number CA039077 awarded by The National Institute of Health. The United States government has certain rights in the invention.

1. INTRODUCTION

The present invention relates to novel methods for detection and isolation of cancer cells with metastatic potential from blood, ascites and tumor tissue derived from subjects with metastatic cancer. The invention further relates to novel compositions for use as cell-adhesion matrices for detection and isolation of cancer cells and for use as blood filters by subjects having metastatic cancers. The methods and compositions of the invention may also be used in assays designed for measuring the metastatic potential of isolated cancer cells and for identification of agents having anti-metastatic potential. In addition, the invention relates to inhibiting the metastatic potential of cancer cells by modulating the activity of serine integral membrane proteases expressed on the surface of metastasizing cancer cells. The present invention is based on the discovery that carcinoma cells isolated from patients' blood, ascites or tumor preferentially adhere to, degrade and ingest collagenous matrix materials. Further, it was discovered that a serine integral membrane protease (SIMP) consisting of seprase and dipeptidyl peptidase IV (DPPIV) subunits are activated on the surface of migrating cells.

2. BACKGROUND OF THE INVENTION

Problems associated with cancer cell separation from the ' or tissue of patients with metastatic cancer during traditional bone marrow harvest and leukopheresis procedures have been reported (Campana, D. et al. Detection of Minimal Residual Disease in Acute Leukemia: Methodologic Advances and Clinical Significance, *Blood,* 1995 Mar. 15, 85 (6): 1416-34; Brugger, W. et al., Mobilization of Tumor Cells and Hematopoietic Progenitor Cells into Peripheral Blood of Patients with Solid Tumors, *Blood,* 83 (3): 636-40, 1994). It is estimated that among the order of 10 billion total mononuclear cells harvested from a patient, there are 25 thousand to 12 million contaminating cancer cells. These contaminating cancer cells have been shown by genetic marking to contribute to relapse (Rill, E R et al., Direct Demonstration that Autologous Bone Marrow Transplantation for Solid Tumors Can Return a Multiplicity of Tumorigenic Cells, *Blood,* 84 (2): 380-383, 1994).

Large numbers of cancer cells were also found in the circulation of cancer patients with metastatic diseases. Glaves, D., R P Huben, & L. Weiss (1988. Br. J. Cancer. 57:32-35) took samples of blood from the renal vein in 10 patients just prior to surgery of renal cell carcinoma and estimated that cancer cells were being released at rates of $10^7$ to $10^9$ cells per day. How these circulating cancer cells contribute to metastasis remains unknown. A major stumbling block is the difficulty involved in identifying an extremely minor subpopulation of circulating cancer cells, ranging from one of thousands to millions of cells, which are metastatic. It is apparent that majority of circulating cancer cells are killed due to host immunity. For examples, in experimental animal tumor models where the use of antibody-based cell separation is more reliable, it has been estimated that about 10 to 100 million tumor cells are released into the blood during the growth of transplantable B16 melanomas and Lewis lung tumors (approximately 20 days), however, these cells give rise to less than 100 lung metastases per mouse (Glaves, D., 1983, Br. J. Cancer, 48:665-673). Furthermore, in the large number of experiments in which tumor cells have been introduced directly into the circulation of mice or rats it is rare that more than 0.01% of such cells form tumor nodules. More commonly the efficiency is two or more orders of magnitude lower. These experimental data suggest that the initial release of cancer cells from the primary tumor is not the limiting factor in metastatic development as only a very small fraction of shed cancer cells are viable, invasive, and, therefore, metastatic. It is essential to develop a cell separation and detection system targeting on such metastatic cells for the understanding of mechanism of metastasis.

Several methods are known for separating cancer cells from blood or body fluids. Such methods include, for example, separating cancer cells one by one by microdissection (Suarez-Quian et al., 1999, *Biotechniques,* 26:328-35; Beltinger and Debatin, 1998, *Mol. Pathol* 51:233-6) or by antibody-based methods using fluorescence activated cell sorting (Pituch-Noworolska et al., 1998, *Int. J. Mol. Med.* 1:573-8), separating cancer cells coated with antibodies on a magnetic material through the use of a magnetic field (Denis et al., 1997, *Int. J. Cancer* 74:540-4; Racila et al., 1998, *Proc. Natl. Acad Sci USA* 95-4589-94), or separating circulating cancer cells on density gradients (Sabile et al., 1999, *Am. J. Clin. Pathol.* 112:171-8). However, such cancer cell separation methods are dependent on the availability of tumor specific antibodies or the buoyant density and morphology unique to different cancer cells. Thus, a great need exists for efficient methods for removing cancer cells from a hematopoietic cell transplant (Gulati, S C et al. Rationale for Purging in Autologous Stem Cell Transplantation. *Journal of Hematotherapy,* 2 (4):467-71, 1993).

As demonstrated in early studies, primary cancers begin shedding neoplastic cells into the circulation at an early stage of metastases formation (Fidler I J, 1973, *European Journal of Cancer* 9:223-227; Liotta L A et al., 1974, *Cancer Research* 34:997-1004). Once shed into the circulation, cancer cells adhere to the basement membrane underlying vessel walls and invade adjacent connective tissue leading to formation of micrometastases (Liotta et al., 1991, *Cell* 64:327-336). It is postulated that cancer cells present in the invasion front and those shed into the circulation are critically involved in the progression of metastatic diseases.

The metastatic process is complex, involving escape of a cancer cell from the primary tumor, movement to a new location and establishment of growth at the new site. To successfully metastasize, the invasive cancer cells must acquire the following metastatic properties: (i) shedding from primary carcinoma, (ii) survival in the circulation and growth on vessel wall, (iii) the ability to invade (adhere to, and subsequently degrade and ingest) collagenous matrix, and (iv) extravasation, colonization and cooperation with angiogenesis (Chambers et al., 1998, *Cancer & Metastasis Review* 17:263-269).

The various steps associated with the process are essentially the same whether the cell escapes into lymphatic or blood vessels, and they involve an essential cellular property, i.e., cell invasiveness. Cancer invasiveness requires the adhesion to, and the degradation and ingestion of the extracellular matrix (ECM) by invading cancer cells, accompanied by translocation or migration of the cells into the ECM. Such cellular activities occur on membrane protrusions referred to as invadopodia, which exhibit dynamic membrane mobility, ECM adhesion, and degradation. Recent evidence has demonstrated the involvement of serine integral membrane proteases (SIMP), including dipetidyl peptidase IV (DPPIV)/CD26 and seprase, in cell surface proteolysis (Chen, W-T, 1996, *Enzyme Protein* 49:59-71).

SIMP members are type II transmembrane proteins comprising cytoplasmic tails that contain 6 amino acids followed by a 20 (seprase) or 22 (DPPIV) amino acid transmembrane domain at the N-terminus and a stretch of 200 amino acids at the C-terminus that constitutes a catalytic region with the catalytic serine in a non-classical orientation (Goldstein, L A et al., 1997, *Biochem. Biophys. Acta.* 1361:11-19). DPPIV specifically removes N-terminal dipeptides from oligo-peptides with either L-proline, L-hydroxyproline, or L-alanine at the penultimate position. Such peptides include Neuro-Peptide Y and other peptide hormones (Heins, J et al., 1988, *Biochim. Biophys. Acta* 954:161-169; Walter, R et al., 1980, *Mol. Cell Biochem.* 30:111-126). In addition, a recent report showed that DPPIV also possesses a seprase-like gelatinase and endopeptidase activity, suggesting its involvement in collagen degradation (Bermpohl F et al., 1998, *FEBS Letters* 428:152-156). In addition, DPPIV is expressed constitutively on brush border membranes of intestine and kidney epithelial cells (Yaron and Naider, F, 1993, *Crit. Rev. Biochem. Mol. Biol.* 28:31-81; Morimoto C. and Schlossman S F, 1994, *Immunologist* 2:4-7) and transiently expressed on T-cells implicating DPPVI as a marker for T-cell activation (Morimoto C. and Schlossman S F, 1994, *Immunologist* 2:4-7).

Seprase, originally identified as a 170-kDa membrane-bound gelatinase is expressed on invadopodia of highly aggressive melanoma LOX (Aoyama A. and Chen, W. T., 1990, Proc. Natl. Acad. Sci. U.S.A. 87:8296-8300; Mueller, S C et al., 1999, J. Biol Chem. 274:24947-24952; Monsky, W L et al., 1994, *Cancer Res.* 54:5702-5710). The active enzyme was isolated from cell membranes and shed vesicles of LOX cells. Seprase is a homodimer of 97-kDa subunits (Pineiro-Sanchez, M L et al., 1997, *J. Biol. Chem.* 272:7595-7601). Analysis of the deduced amino acid sequence derived from a cDNA that encodes the 97-kDa subunit reveals that the 97-kDa subunit is homologous to DPPIV, and is essentially identical to fibroblast activation protein α (FAPα) (Goldstein et al., 1997 *Biochem. Biophys. Acta.* 1361, 11-19; Scanlon, M. J et al., 1994, *Proc. Natl. Acad. Sci. U.S.A.*, 91:5657-5661). FAP α is expressed on reactive stromal fibroblasts of epithelial cancers and in healing wounds but not in adult tissue (Garin-Chesa, P. et al., 1990, *Proc. Natl. Acad. Sci. U.S.A.* 87:7235-7239).

In carcinoma tumors, however, FAPα was not found to be expressed in carcinoma or endothelial cells (Garin-Chesa et al., 1990, *Proc. Natl. Acad. Sci.* 87:7235-7239). Seprase and FAPα differ mainly in a stretch of 45 amino acid residues contiguous with the highly conserved motif GXSXG that contains the active site serine (Scanlan et al., 1994, *Proc. Natl. Acad. Sci. USA* 91:5657-5661; Goldstein et al., 1997 *Biochem. Biophys. Acta.* 1361, 11-19). Recently, an alternatively spliced seprase mRNA was identified from the human melanoma cell line LOX that encodes a novel truncated 27-kDa seprase isoform, that precisely overlaps the carboxyl-terminal catalytic region of 97-kDa seprase (Goldstein and Chen, 2000 *J. Biol. Chem.* 275:2554-2559). The splice variant mRNA is generated by an out-of-frame deletion of a 1223-base pair exonic region that encodes part of the cytoplasmic tail, transmembrane, and the membrane proximal-central regions of the extracellular domain (Val(5) through Ser(412)) of the seprase 97-kDa subunit. It is possible that seprase exhibits both gelatinase and Gly-Pro-dipeptidase activities, while the truncated seprase only has the latter dipeptidase activity.

It has long been believed that collagen remodeling is mediated by matrix metalloproteinases (MMP). However, trials with MMP inhibitors (Marimastat, AG3340) and angiogenic inhibitors (angiostatin and endostatin) in patients with cancer have not produced obvious evidence of anti-metastatic, anti-invasive effects. These data indicate that other enzyme systems are needed to replace MMP at the invasion front of a tumor.

Cancer cell invasiveness in vitro can be a direct indication of a tumor's metastatic potential. Knowledge of the cell's invasive phenotype is important in developing cancer treatments that maximize patient survival and quality of life. It is also important in its use in formulating diagnostic tools for detecting cancer progression and metastasis. Therefore, much effort has focused on measuring cancer cell invasiveness, a characteristic of the metastatic potential of carcinomas.

Invasiveness of a cell is often inferred by its cell surface proteolytic activities that degrade extracellular matrix (ECM) components, and that internalize ECM fragments. In vitro assays for such activities are often complicated by other cell surface phenomena such as adhesion, cell surface proteolysis, and membrane mobility. One particular assay designed to measure invasiveness of a cell involves the covalent linkage of fluorescence-labeled or radio labeled fibronectin (or other ECM components) to the surface of a cross-linked gelatin substrata (Chen et al., 1984, *J. Cell Biol* 98:1546-1555; Chen, et al., 1985, *Nature*, 316:156-158; Chen et al., 1989, *J. Exp. Zool.* 251:167-185; Chen et al., 1994, *J. Tiss. Cult. Meth.* 16:177-181; Meuller et al., 1989, *J. Cell. Biol.* 109:3455-3464). In this particular technique fibronectin was labeled and used to coat over-fixed protein film. The film was then used to measure cell surface proteolytic activities as well as the cellular invasive phenotype in terms of foci of invadopodial extensions and surface indentations in the film. However, this fibronectin-gelatin film assay is of limited value because (i) it uses conventional, over-fixed protein films; (ii) it lacks sensitivity for detecting proteolytic activity of moderately invasive cells such as most tumor cell lines in culture, fibroblasts and angiogenic endothelial cells, (iii) cross-linked gelatin fragments are not ingested by cancer cells; and (iv) it is difficult to build a three dimensional culture gel system from fibronectin and cross-linked gelatin materials. Thus, reliable procedures to measure the invasiveness of such cells will have significant impact in both clinical diagnostic and therapeutic applications of cancer.

The present invention provides a unique, functional based cell separation method to isolate various forms of cancer cells from blood, ascites and primary tumor tissue of patients with metastases, and peripheral blood mononuclear cells including endothelial cells from blood of normal donors. Additionally, the present invention provides evidence that seprase and/or DPPIV are selectively induced in invasive carcinoma cells and in activated fibroblasts (or other tissue cells) and sprouting endothelial cells of malignant tissues thereby providing targets for development of drugs for inhibiting tumor invasion and metastasis.

3. SUMMARY OF THE INVENTION

The present invention relates to a novel cancer cell capture system for rapid and efficient detection and selection of invasive cancer cells from the blood, ascites and/or tissue of cancer patients. In later stage cancer patients, some cancer cells were found associated with blood components to form large aggregates of cells. Such clumping of cells may contribute to organ dysfunction associated with late stage cancer. The present invention provides compositions and methods that can detect such cells in the blood of cancer patients with metastatic diseases, and may be used to remove such aggregates of cells as well as free-living individual cancer cells from the patient's blood, ascites and/or tissue.

In contrast to earlier antibody approaches for cancer cell isolation and detection, the present cell separation system is based on the functional properties of the cancer cells, i.e., their ability to adhere to, degrade, and ingest the extracellular matrix. Thus, the cell separation and assay system of the prevent invention is designed to identify and isolate the very small fraction of cancer cells in the blood, ascites and tumor tissue of cancer patients that are viable, invasive and metastatic. The enriched cancer cell population can be used, for example, to determine their metastatic potential and the most effective treatment regime. The enriched cells may also be used in fusions with dendritic cells for cancer vaccine development.

The invention relates to natural fibrous compositions comprising blood-borne adhesion molecule-coated collagen, fibrin, cotton and plastic fibers, to be used as cell-adhesion matrices for use as blood filters by subjects having metastatic cancers. Type I collagen derived from, for example, placental tissues or rat-tail, is particularly useful for formation of the matrix which can be readily assembled into any form and be coated on vessel surfaces through cycles of polymerization and de-polymerization. The collagen matrix is coated with a variety of different adhesion molecules derived from blood, including but are not limited to fibronectin, laminin and vitronectin. Adhesion of individual cancer cells or cell clusters to such a cell-adhesion matrix provides a basis for cellular isolation.

The compositions can be used, for example, to remove undesired cancer cells and to enrich hematopoietic progenitor cells from the blood or bone marrow for use as donor cells in bone marrow transplantation. Further, specific cancer cells of different carcinoma cancers may be enriched from whole blood by the cell separation methods of the present invention, subjected to ex vivo expansion, then used to interact with dendritic cells to develop an effective tumor vaccine. In addition, circulating cancer cells could be isolated from the patient and then subjected to a battery of chemotherapeutic regimes in vitro. Effective doses or drug combinations could then be administered to that same patient.

The compositions and methods of the invention provide a rapid method for detection and isolation of invasive cancer cells in blood, ascites and tissues of patients with cancer. Such cancers include, but are not limited to, prostate, breast, colon, lung, head & neck, brain, bladder, lymphoma, ovarian, renal & testis, melanoma, liver, pancreatic or other gastrointestinal cancers. Cancer cells are detected and characterized using the immunocytochemistry and cellular functional assays of the invention, i.e., collagen degradation and ingestion.

The method of the invention can be used to develop sensitive assays for the determination of invasive cancer cells in the blood, ascites or tumor tissue of cancer patients for use in prognostication, monitoring therapeutic and surgical treatments and early detection of cancer. The sensitivity and accuracy of measuring the metastatic potential of a cancer may be further enhanced using additional assays known to those of skill in the art, such as determining the tissue origin of cancer cells, measuring the angiogenic capability of the cells, and determining reduced leukocyte or complement association.

The cell-adhesion matrix of the invention also provides a cancer cell trap that allows for the high yield and efficient removal of viable cancer cells from whole blood, buffy coat, peripheral blood stem cell preparation or bone marrow. The cell separation method of the invention is intended for use in therapeutic apheresis and leukopheresis, in which autologous blood transfusions are done from which contaminating cancer cells have been removed. The present invention provides a highly efficient method for removal of cancer cells from whole blood of patients with prostate, breast, colon, lung, head & neck, brain, bladder, lymphoma, ovarian, renal & testis, melanoma, liver, or pancreatic and other gastrointestinal cancers.

Assays are also provided that may be used to screen for agents capable of inhibiting metastasis, thereby modulating the metastatic potential of cancer cells. Such assays involves contacting the cell-adhesion matrix with a cancer cell sample in the presence of a test agent and subsequent detection and quantitation of cancer cell adhesion to and degradation or ingestion of the matrix. The assay system of the invention can also be used to monitor the efficacy of potential anti-cancer agents during treatment. For example, the metastatic potential of cancer cells in whole blood can be determined before and during treatment. The efficacy of the agent can be followed by comparing the metastatic potential of the cancer cells throughout the treatment. Agents exhibiting efficacy are those which are capable of decreasing cancer invasiveness, increasing host immunity, and suppressing cancer proliferation, but having little or no effect on normal tissue cells. For example, such an anti-metastatic drug screening assay system has identified monoclonal antibodies and peptide inhibitors directed against seprase-DPPIV complex that block the ability of migratory cells to adhere, degrade, and invade a collagenous matrix (FIGS. 13 and 14). Furthermore, such assay system demonstrates that anti-sense and ribozyme constructs against seprase and DPPIV are capable of decreasing the invasiveness of breast carcinoma cells (FIG. 19).

Methods and compositions are provided for inhibiting the metastatic potential of cancer cells comprising the administration of modulators of serine integral membrane proteases. This aspect of the invention is based on the observation that formation of a novel protease complex, comprising seprase and DPPIV, is a prerequisite for cell invasion into the collagen matrix. Such protease inhibitors include but are not limited to those capable of inhibiting the activity of DPPIV and seprase. The discovery that activation of seprase and DPPIV activity is a prerequisite for cell invasion and migration provides target molecules for drug screening assays designed to identify inhibitors of cancer cell migration.

4. BRIEF DESCRIPTION OF THE DRAWINGS

Figure 1B:
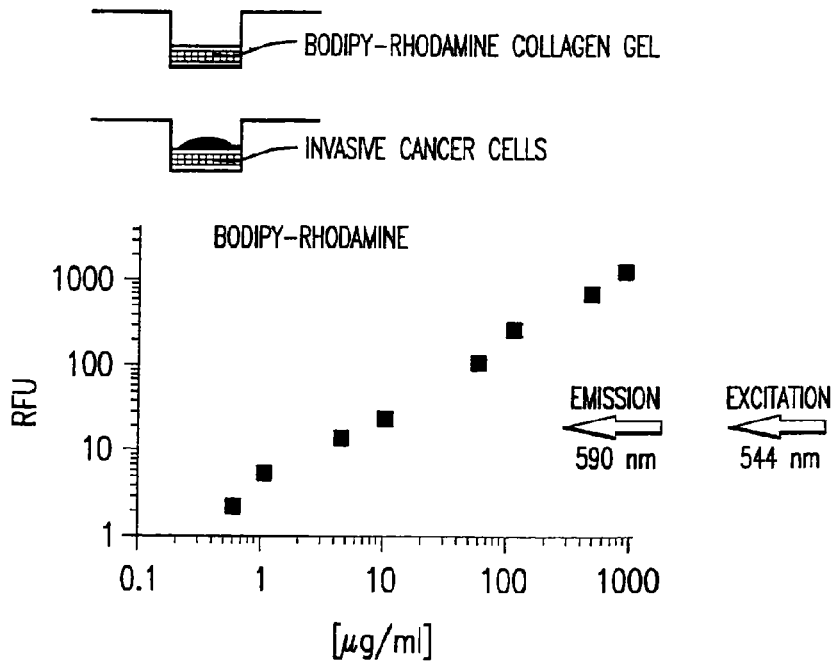

FIG. 1A-B. Composition and preparation of a cell-adhesion matrix. FIG. 1A. Preparation of the type I collagen based, cell-adhesion matrix, illustrating seven steps involved in matrix preparation, cell separation, and microscopic measurement of the invasiveness of a cancer cell. FIG. 1B. Utilization of the type I collagen based, cell-adhesion matrix in microtiter measurement of overall collagen degradation by the cells. The degradation and ingestion of the Bodipy-rhodamine collagen matrix by cancer cells are measured with a fluorescent microtiter plate reader as an increase in red fluorescence. The bottom graph shows release fluorescence unit (RFU) is proportional to the amount of Bodipy-rhodamine collagen overlaid on each microtiter well in the presence of bacterial collagenase at 37° C. for 30 minutes.

FIG. 2A-B. Diagnostic and therapeutic applications of the cell-adhesion matrix based, cell separation and assay system. FIG. 2A. Cross-sectional views of cell separation and assay methods that may be used for diagnostic applications, including diagnostics, monitoring therapeutic or surgical responses, and early cancer detection. The steps of isolating, detecting and characterizing cancer cells from blood, ascites or tissue cell populations is illustrated. FIG. 2B. Cross-sectional views of cell separation and assay methods of the present invention that may be used for therapeutic and preventive applications. The steps of isolating and culturing cancer cells from blood, ascites or tissue cell populations are illustrated.

FIG. 3A-F. Cancer cell separation analyses of blood samples from patients and controls. Representative examples of fluorescent-tagged Hs578T breast carcinoma cells spiked in complete medium alone, or the blood of control normal donor and a bladder cancer (BLC) patient are shown. Red fluorescent-tagged Hs578T breast carcinoma cells were added to 3-ml of medium or blood samples, the cells were captured by a collagenous matrix in a microtiter well and cultured for 18 hours. The images shown were taken with super-imposed illumination of fluorescence and phase contrast, and represent only a portion of the microtiter well. FIG. 3A. Fluorescent analysis of Hs578T breast carcinoma cells (500 cells) added to the medium alone. Estimated 495 cells were found as bright spots attached and spread on the matrix. FIG. 3B. Fluorescent analysis of Hs578T breast carcinoma cells (500 cells) spiked in the blood of a normal donor. Estimated 415 red fluorescent carcinoma cells were found among the other blood cells (without fluorescent signal) in the culture that remained on the matrix substratum. FIG. 3C. Fluorescent analysis of Hs578T breast carcinoma cells (19 cells) spiked in the blood of a normal donor. Estimated 11 red fluorescent carcinoma cells were found among the other blood cells (without fluorescent signal) in the culture that remained on the matrix substratum. FIG. 3D. Fluorescent image of Hs578T breast carcinoma cells (200 cells) spiked in the blood of a BLC patient. Estimated 182 Hs578T breast carcinoma cells along with circulating BLC cells were captured from blood of cancer patient. Hs578T cells tend to form aggregates with mononuclear blood cells of the patient seen as dark spots in this figure. FIG. 3E. Fluorescent analysis of matrix-captured Hs578T breast carcinoma cells (19 cells) spiked in the blood of a BLC patient. Estimated 16 red fluorescent carcinoma cells were found among the other blood cells and one Hs578T breast carcinoma cell is seen in the field. FIG. 3F. Immunofluorescent analysis of matrix-captured Hs578T breast carcinoma cell shown in FIG. 3E and circulating BLC cells. Here, the Hs578T breast carcinoma cell and four bladder carcinoma cells derived from the blood were stained with fluorescein-conjugated anti-cytokeratins PCK antibody. The Hs578T breast carcinoma cell (shown as red fluorescence in FIG. 4E) can be seen among the green fluorescent cytokeratin-labeled bladder carcinoma cells derived from patient's blood. Picture size A-D, 662 µm×478 µm; Picture size E-F, 331 µm×239 µm.

Figure 4C:
Figure 4F:
Figure 4B:
Figure 4E:
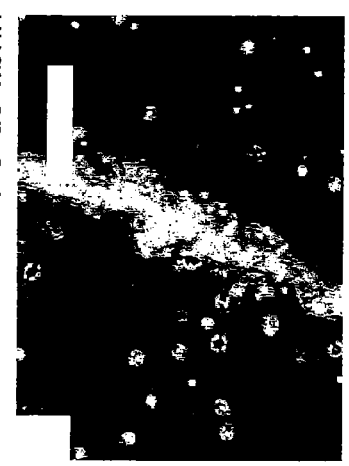
Figure 4A:
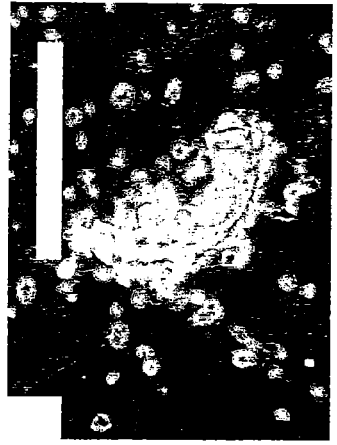
Figure 4D:
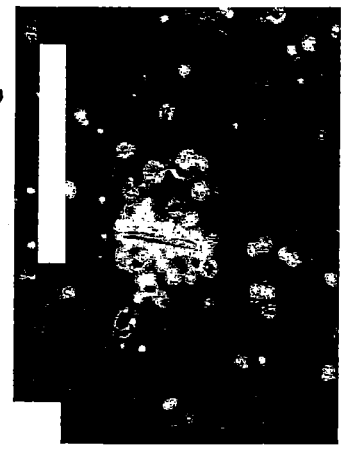
Figure 4I:
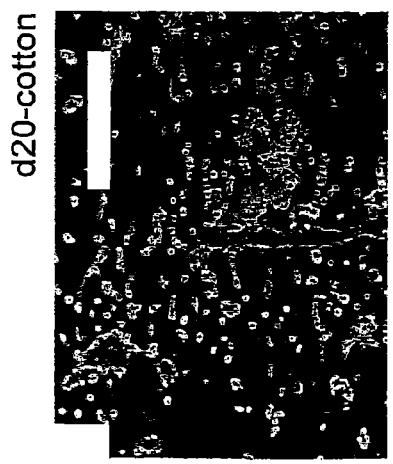
Figure 4H:
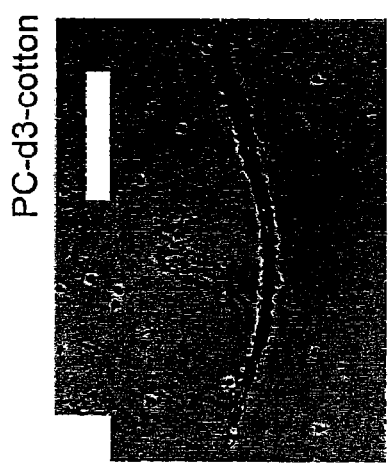
Figure 4G:
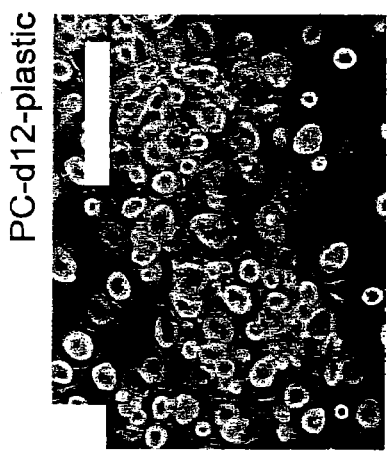

FIG. 4A-I. Circulating cells attached to cell-adhesion matrix. FIG. 4A-C. Circulating cells aggregated on a piece of tissue fragment in blood of a patient with squamous cell carcinoma of head and neck (HN). The cell-tissue cluster was captured on the substratum using a collagenous matrix, and cultured for four days (d4 in A), six days (d6 in B), and 13 days (d13 in C). FIG. 4D. Cells aggregated on a piece of tissue fragment in blood of a patient with metastatic prostate cancer (PC), and cultured for three days (d3). FIG. 4E. Circulating carcinoma cells from a patient with metastatic prostate cancer (PC) aggregated on a fibrin fiber (fibrin), and cultured for three days (d3). FIG. 4F. Circulating cells from a patient with metastatic prostate cancer (PC) aggregated on plastic scraps (plastic), and cultured for three days (d3). Putative cancer cells of large size can be seen to preferentially adhere on plastic scraps in the field. FIG. 4G. Circulating cells in the same culture as in F, but cultured for twelve days (d12). Putative cancer cells of large size can be seen to preferentially adhere on plastic scraps in the field. FIG. 4H. Circulating cells from a patient with metastatic prostate cancer (PC) aggregated on purified cotton (cotton), and cultured for three days (d3). FIG. 4I. Growth of putative cancer cells from a patient with brain cancer (BN) aggregated on purified cotton (cotton), and cultured for 20 days (d20). Picture size A-G, 662 µm×478 µm; Picture size H-I, 1324 µm×956 µm.

Figure 5A:
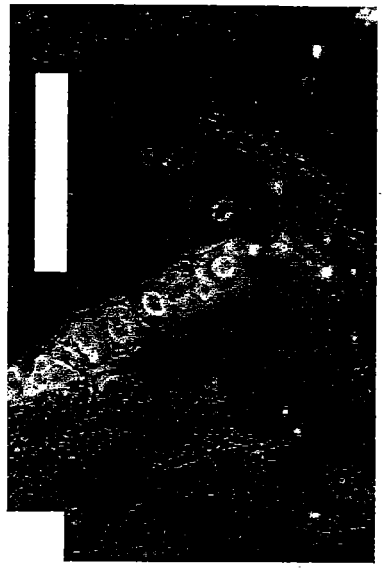
Figure 5B:
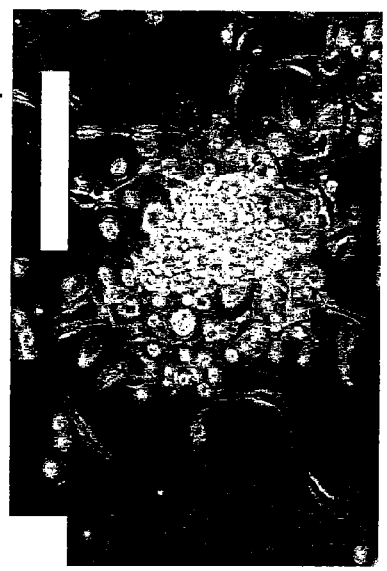
Figure 5C:
Figure 5D:
Figure 5F:
Figure 5H:
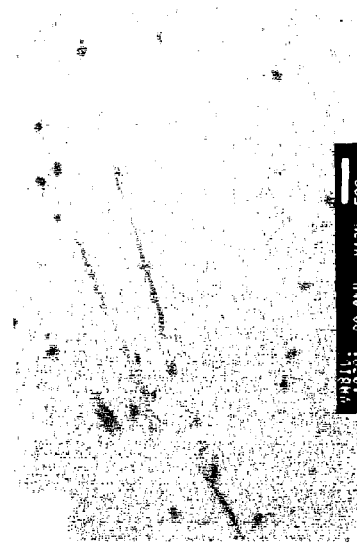
Figure 5E:
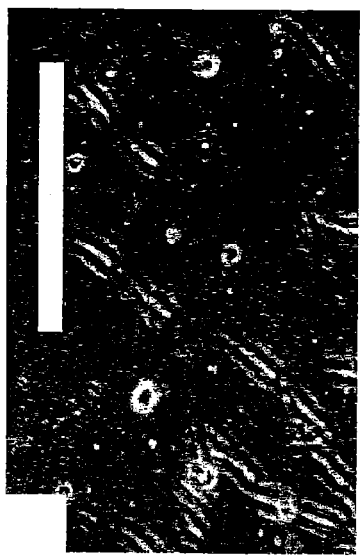
Figure 5G:
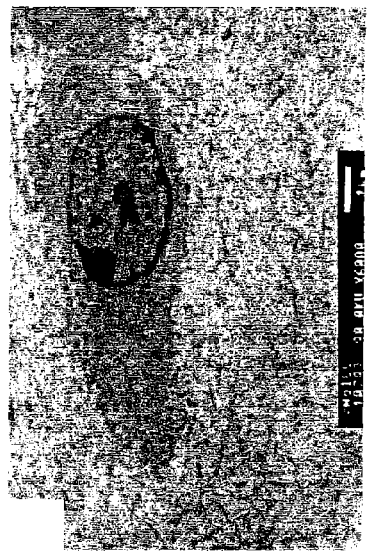

FIG. 5A-H. Circulating cells attached to type I collagen-based, cell-adhesion matrix. FIG. 5A-C. Cell aggregates from a patient with metastatic pancreatic cancer (PnC) captured on the substratum using the type I collagen matrix, washed, and cultured for five days (A), nine days (B), and 16 days (C) on the matrix. These illustrate phase-microscopic appearance of a type I collagen based, cell-adhesion matrix and carcinoma cells, that invade the matrix and grow on the plastic surface. Carcinoma cells, not present in blood of most normal donors, have distinct morphology and increase their cellular size and number in culture, while co-isolated leukocytes are small and reduce their number in culture. FIG. 5D. Circulating cell aggregates from a patient with metastatic pancreatic cancer (PnC) captured on the substratum using the type I collagen matrix. Cells were eluted from the matrix and cultured in complete medium for seven days on plastic surface (plastic). Spindle-shaped cells associate with epithelial-shaped, carcinoma cells at the periphery of a cellular colony. FIG. 5E-F. Invasion of stromal fibroblasts into a type I collagen substratum. Cells were dissociated and isolated from a tumor biopsy of a patient with squamous cell carcinoma of head and neck (HN). Two morphologically distinct, cell types were isolated on the surface of the matrix: HN squamous cells remain quiescent on the matrix surface (E), while stromal fibroblasts invade into the collagen gel (F), approximately 80 µm below the level seen in FIG. 5E as measured by the fine stage adjustment dial of Nikon Eclipse TE300 inverted microscope. FIG. 5G. Morphology of a type I collagen based, cell-adhesion matrix illustrating transmission electron-microscopic appearance of the matrix and its adherent cancer cells, that were isolated from the blood of a patient with metastatic colon cancer (CC). FIG. 5H. A high magnification view of the collagen fibers shown in FIG. 5H, illustrating transmission electron-microscopic appearance of the assembled collagen fibers. Picture size A-F, 662 µm×478 µm; Picture size G-H, indicated in the bar area.

Figure 6A:
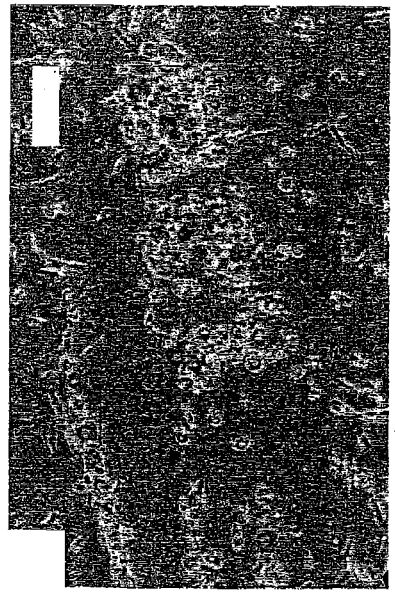
Figure 6B:
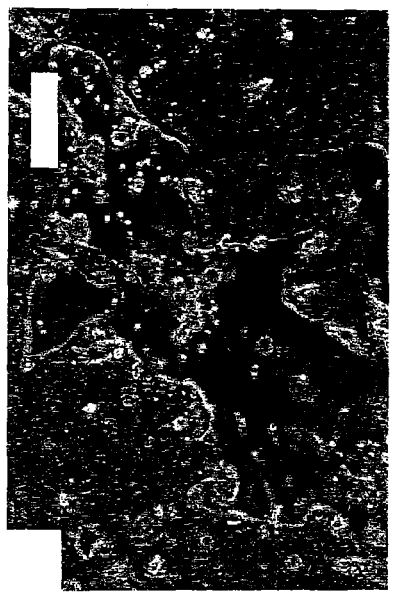
Figure 6C:
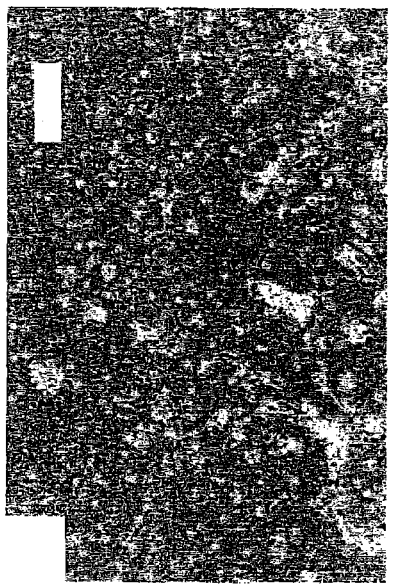
Figure 6D:
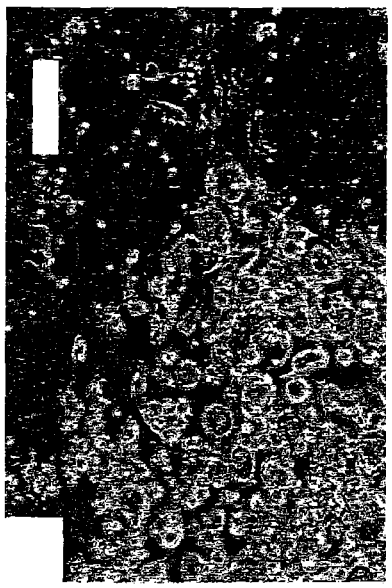

FIG. 6A-D. Morphological basis of the invasive phenotype of circulating carcinoma cells. FIG. 6A-B. Circulating cell aggregates from a patient with metastatic colon cancer (CC). Cells were freshly isolated and cultured for one day (d1) and nine days (d9). These illustrate phase-microscopic appearance of degraded holes in the type I collagen based, cell-adhesion matrix generated by carcinoma cells and characteristics of carcinoma cells, that have distinct morphologies, i.e., small in size on d1 (A) but large and epithelial shape on d9 (B). Carcinoma cells increase their cellular size and number in culture, while co-isolated leukocytes are small and reduce their number. Also, spindle-shaped cells associate with epithelial-shaped, carcinoma cells in colonies (B). FIG. 6C-D. Circulating cell aggregates from a patient with metastatic stomach cancer (SC). Cells were captured on the substratum using the type I collagen matrix, and cultured for 19 days. Epithelial-shaped, carcinoma cells grow on plastic surface in degraded holes of collagenous film (C) or line the edge of collagen film (D). Picture size A-B, 1324 µm×956 µm; Picture size C-D, 662 µm×478 µm.

Figure 7B:
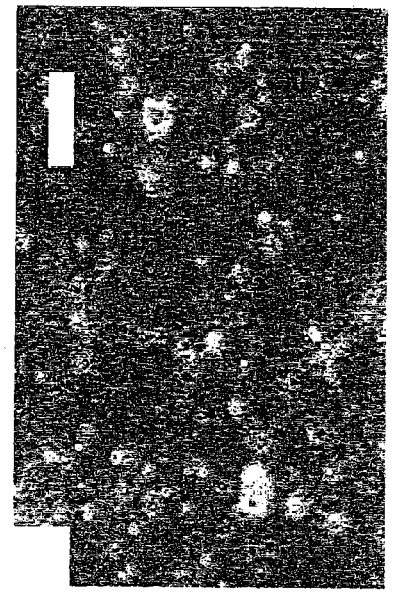
Figure 7D:
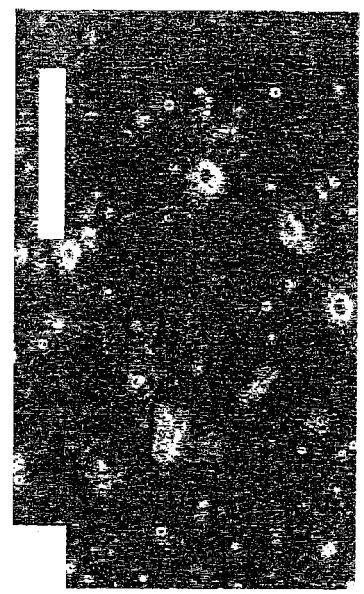
Figure 7A:
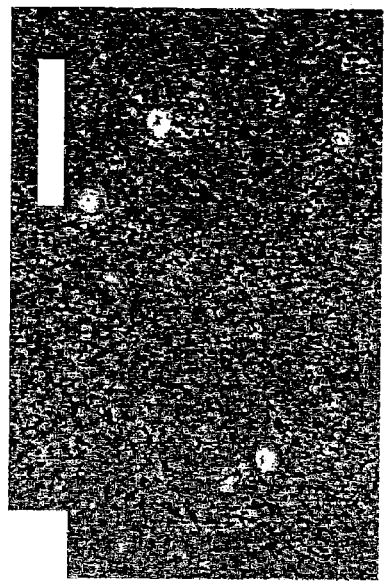
Figure 7C:
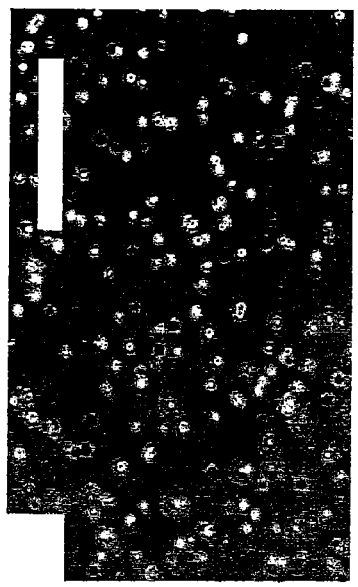

FIG. 7A-D. Cells from control blood samples that are isolated by the cell separation method. FIG. 7A. Cells isolated from the blood of a 39 year-old normal donor and their underlying type I collagen matrix. Very few cells survived after 7 days in culture, while the matrix membrane stayed intact. FIG. 7B. Cells isolated from the blood of a patient with benign colon tumor (CTN) and their underlying type I collagen matrix. Very few cells were isolated, and the matrix membrane stayed intact. FIG. 7C-D. Circulating cells of a patient with metastatic breast cancer (BC) and their underlying type I collagen matrix. Blood sample was collected during treatment with chemotherapeutic compounds. Relatively few cells were isolated and survived in d1 (C) and d4 (D) cultures, and the matrix membrane stayed intact. Picture size A-D, 662 µm×478 µm.

Figure 8I:
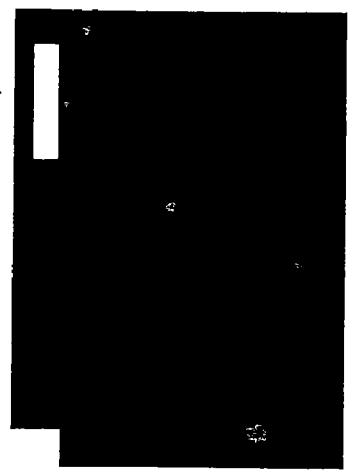
Figure 8H:
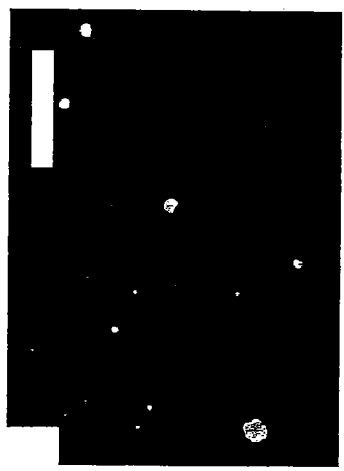
Figure 8G:
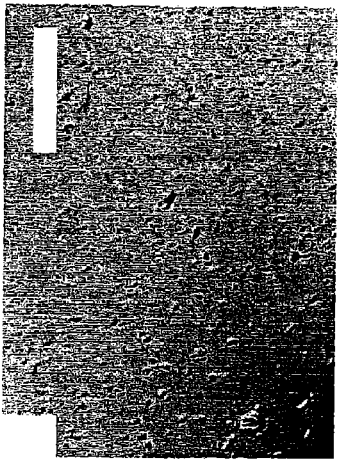
Figure 8L:
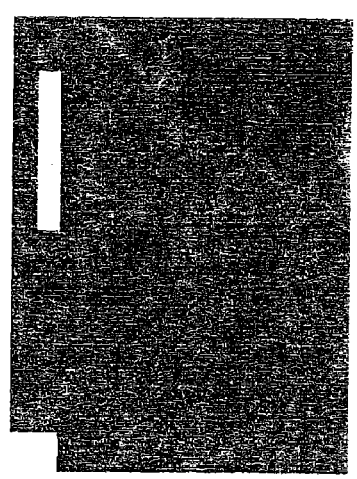
Figure 8K:
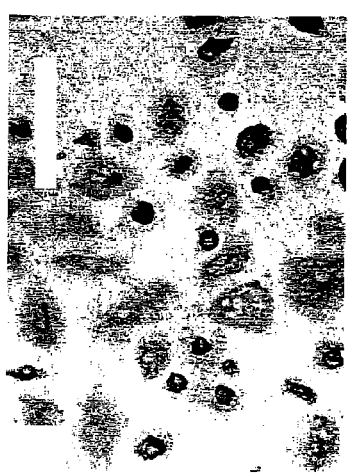
Figure 8J:

FIG. 8A-L. The cell separation and assay system for the cell invasive phenotype using fluorescently labeled collagen, and immunocytochemistry of circulating carcinoma cells using antibodies against epithelial markers. Cells were derived from the blood of patients with breast carcinoma (BC, A-C), squamous cell carcinoma of head-neck (HN, D-F), colon cancer (CC, G-I), prostate cancer (PC, K), and a normal donor (Control, L), as well as the Hs578T breast carcinoma cell line (Hs578T, J). Cells were captured on the substratum using a rhodamine-collagen matrix, and cultured for one day (d1) or 63 days (d63). FIG. 8A-C. Ingested rhodamine-collagen blotch as a marker for the invasive phenotype of circulating carcinoma cells in a patient with breast cancer (BC). Cells were seeded on the matrix for 18 hours and fixed for examination. Among numerous leukocytes in the background, individual and cluster of putative cancer cells (PH, phase contrast image shown in A) were shown to ingest rhodamine-collagen fragments, marked Col+ (red fluorescence shown in B). Super-imposed image shown in panel C demonstrates the exact match of rhodamine-collagen spots to putative cancer cells. These represent the enumeration of 2,067 Col$^+$ cells per ml of patient's blood. FIG. 8D-F. Ingested rhodamine-collagen blotch as a marker for the invasive phenotype of circulating carcinoma cells in a patient with squamous cell carcinoma of head-neck (HN). A large cluster and individuals of putative cancer cells (PH, phase contrast image in D) were shown to be coincident with cells positively antibody-stained for broad-spectrum cytokeratin subunits (PCK$^+$, in E) and these loaded with rhodamine-collagen Col+ (red fluorescence in F). These represent the enumeration of 20,814 PCK$^+$ and 18,003 Col$^+$ cells, respectively, per c.c. of patient's blood. The high number of PCK$^+$ compared to these of Col$^+$ cells may be due to the presence of less viable cancer cells that are positive for antibody staining, and that adhere to the cell-adhesion matrix. FIG. 8G-I. Ingested rhodamine-collagen blotch as a marker for the invasive phenotype of circulating carcinoma cells in a patient with colon cancer (CC). Clusters and individuals of putative cancer cells (differential interference contrast image in G) were labeled with antibodies against epithelial surface antigen (ESA$^+$; stained red in G). ESA$^+$ cells were shown to be coincident with these stained with antibodies against the endothelial marker factor VIII (F8$^+$; green fluorescent cells in H) and these ingested rhodamine-collagen fragment Col+ (red fluorescent cells in I). These represent the enumeration of 2,284 ESA$^+$, 7,308 F8$^+$, and 1,978 Col$^+$ cells, respectively, per ml of patient's blood. The high number of F8$^+$ compared to these of Col$^+$ or ESA$^+$ cells may be due to the presence of normal endothelial cells in the blood. FIG. 8J. The Hs578T breast carcinoma cell line stained with anti-PCK antibodies, as carcinoma (epithelial) marker control. FIG. 8K. PC cells in culture for 63 days (d63) stained ESA$^+$. Note that these large cells contain multiple nuclei and increase their diameter over 5-folds as compared to d1 cells in G. FIG. 8L. Rhodamine-collagen matrix that remains intact after culturing blood cells from a normal donor for one day (d1). Picture size A-C, 1324 µm×956 µm; Picture size D-F, 331 µm×239 µm; Picture size G-L, 662 µm×478 µm.

Figure 9C:
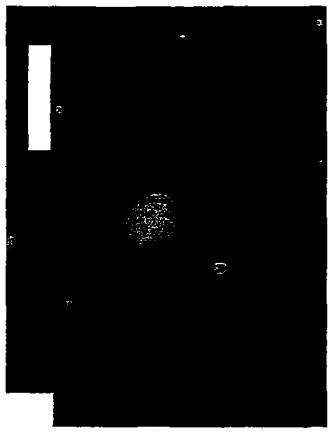
Figure 9F:
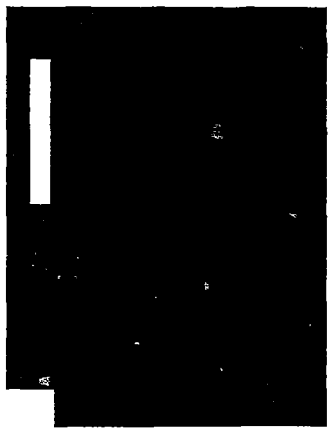
Figure 9B:
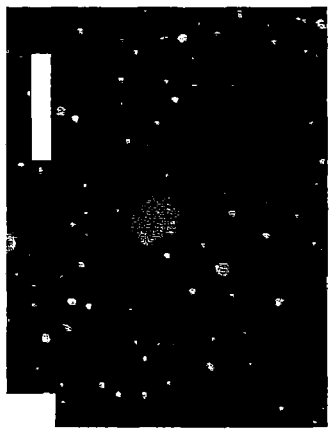
Figure 9E:
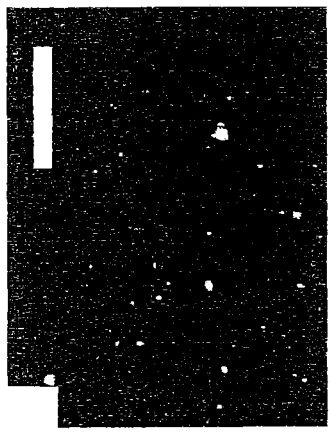
Figure 9A:
Figure 9D:
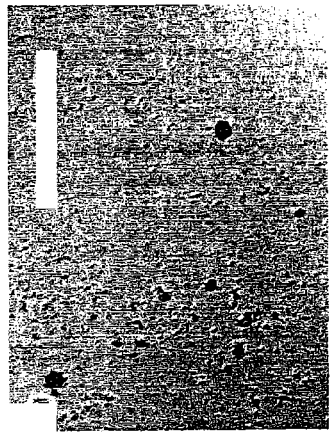
Figure 9I:
Figure 9H:
Figure 9G:
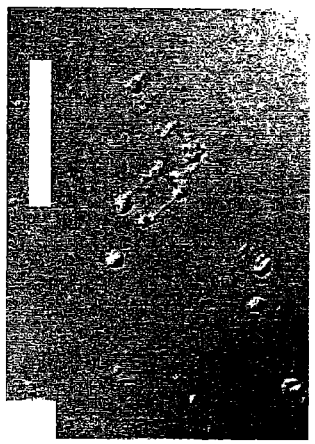
Figure 9L:
Figure 9K:
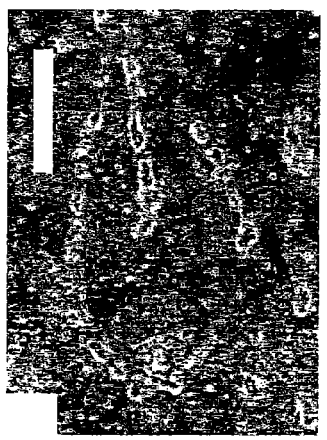
Figure 9J:
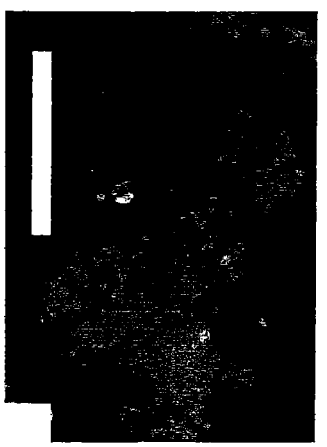

FIG. 9A-L. Angiogenic propensity of circulating carcinoma cells. Cells were derived from the blood of patients with squamous cell carcinoma of head-neck (HN, A-C; I-J), colon cancer (CC, D-F) and prostate cancer (PC, G-H). Cells were captured on the substratum using the collagen matrix, and cultured for 1-11 days as indicated by d1 or d11. FIG. 9A-C. A large cluster and seven individual HN cells (phase contrast image shown in A) that were labeled strongly for F8$^+$ (B) and that ingested collagen fragment Col+ (C). The HN cells shown in phase contrast (PH) image (A) are closely associated with these in the same field that exhibited positive reactivity with F8 antibodies (B) and these ingested rhodamine-collagen matrix (C). These represent the enumeration of 42,495 F8$^+$ and 15,611 Col$^+$ cells, respectively, per c.c. of patient's blood. The high number of F8$^+$ as compared to Col$^+$ cells is due to the presence of F8$^+$ endothelial cells in the blood. FIG. 9D-F. A subset of CD31$^+$ and F8$^+$ cells representing the Col+ CC cells. The cells on the rhodamine-collagen matrix were labeled with antibodies against the endothelial cell marker CD31 and fluorescein conjugated antibodies against the endothelial marker factor VIII (F8). The association of bright red stained CD31$^+$ cells with CC cells was shown in differential interference contrast (DIC) image (D). CC cells in the same field exhibited positive reactivity with F8 antibodies (E) and these ingested rhodamine-collagen matrix (F). These represent the enumeration of 11,693 CD31$^+$, 6,577 F8$^+$ and 2,558 Col$^+$ cells, respectively, per c.c. of patient's blood. The high number of CD31$^+$ and F8$^+$ as compared to Col$^+$ cells is due to the presence of CD31$^+$ and F8$^+$ endothelial cells in the blood. FIG. 9G-H. PC cells incorporating acetylated LDL. The bright red stained epithelial surface antigen (ESA) positive cells shown in differential interference contrast (DIC) image (G) display the ingestion of the fluorescein-LDL (H). These represent the enumeration of 9,744 ESA$^+$ and 34,105 LDL$^+$ cells, respectively, per c.c. of patient's blood. The high number of LDL$^+$ as compared to ESA$^+$ cells is due to the presence of other endothelial cells that incorporate acetylated LDL. FIG. 9I-J. Primary cultured HN cells incorporating acetylated LDL. Note that only one specific cell toward the center incorporate both fluorescein-LDL and rhodamine-collagen as shown in the triple fluorescein-Rhodymenia-Hoechst image (J), suggesting that this cell represents a cell retaining the invasive phenotype after in culture for 12 days. FIG. 9K-L. Capillary network development by circulating CC cells on collagen gel. Network formation (K)

and cord-like structures (L) were observed 2 days after plating circulating CC cells on type I collagen gel, 0.5-mm in thickness. Picture size A-C; G-J, 331 μm×239 μm; Picture size D-F; K-L, 662 μm×478 μm.

Figure 10C:
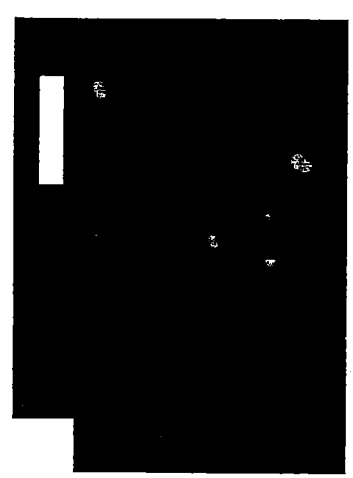
Figure 10F:
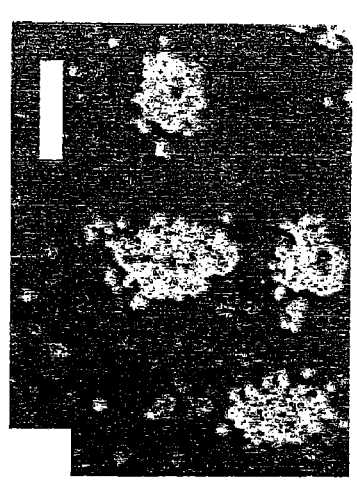
Figure 10B:
Figure 10E:
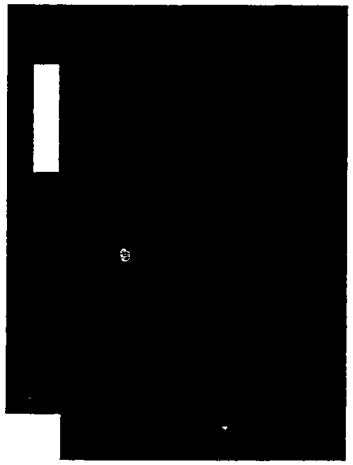
Figure 10A:
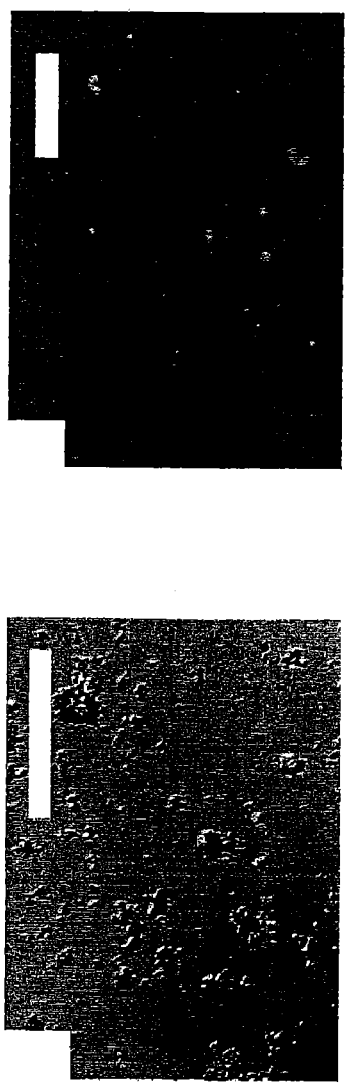
Figure 10D:
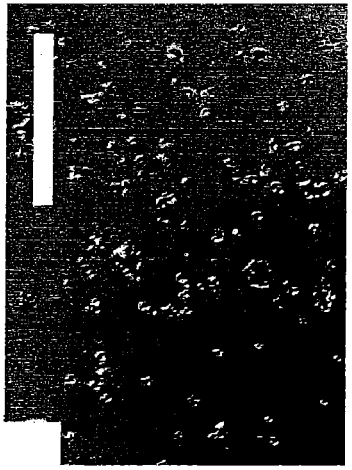
Figure 10I:
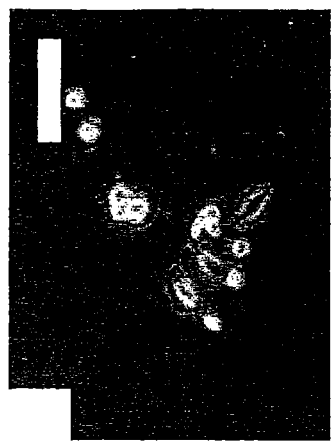
Figure 10L:
Figure 10H:
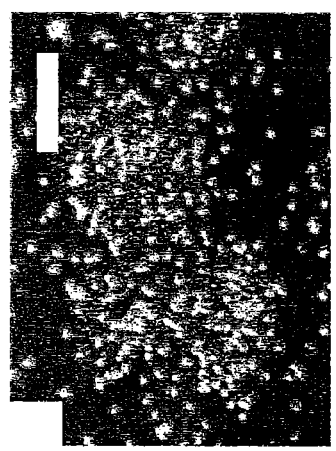
Figure 10K:
Figure 10G:
Figure 10J:

FIG. 10A-L. Immune cancer killing and growth of circulating cancer cells in culture. Cells were isolated from the blood of patients with colon (CC, A-E), prostate (PC, F-I), or bladder cancer (BLC, J-L) using the collagen matrix, and cultured in the medium containing 10-20% human plasma. FIG. 10A-C. $CD34^+$ peripheral blood stem cells clustering with the $F8^+/Col^+$ CC cells. The association of bright red stained $CD34^+$ cells with CC cells was shown in the differential interference contrast (DIC) image (A). CC cells in the same field exhibited positive reactivity with F8 antibodies (B) and these ingested rhodamine-collagen (C). These represent the enumeration of 111,082 $CD34^+$, 7,673 $F8^+$ and 2,558 $Col^+$ cells, respectively, per c.c. of patient's blood. The high number of $CD34^+$ and $F8^+$ as compared to $Col^+$ cells is due to the presence of $CD34^+$ stem cells and $F8^+$ endothelial cells in the blood. FIG. 10D-E. $CD45^+$ leukocytes clustering with the Col+ CC cells. The isolated cells on the rhodamine-collagen matrix were labeled with antibodies against the leukocyte common antigens CD45. The association of bright red stained $CD45^+$ leukocytes with CC cells was shown in the DIC image (D). CC cells in the same field exhibited the ingestion of the rhodamine-collagenous matrix (E). These represent the enumeration of 125,670 $CD45^+$ leukocytes and 1,827 $Col^+$ cells, respectively, per c.c. of patient's blood. FIG. 10F-I. Sequential views of cytolysis of immune and cancer cell clusters from a patient with prostate cancer (PC) who exhibited favorable prognosis. Most cancer cells were attacked by leukocytes and became fragmented after one day in culture (F-H). However, leukocytes disappeared after seven days in such culture, leaving behind a few PC colonies (I). FIG. 10J-L. Cytolysis of bladder cancer (BLC) cells due to autoimmune plasma derived from the same patient. BLC cells were cultured in the presence of 10% autologous plasma, derived from the blood of the same cancer patient (au.plasma in J-K), or those from a normal donor (n. plasma in L). BLC cells became lysed and brown in color in the medium containing autologous plasma in the second day (au.plasma in J-K), while they stayed viable for over 6 weeks in the medium containing normal plasma (n.plasma in L), suggesting a role of auto-cancer antibodies in complement cytolysis and signifying the host immunity against metastasis. Picture size A-L, 662 μm×478 μm.

Figure 11A:
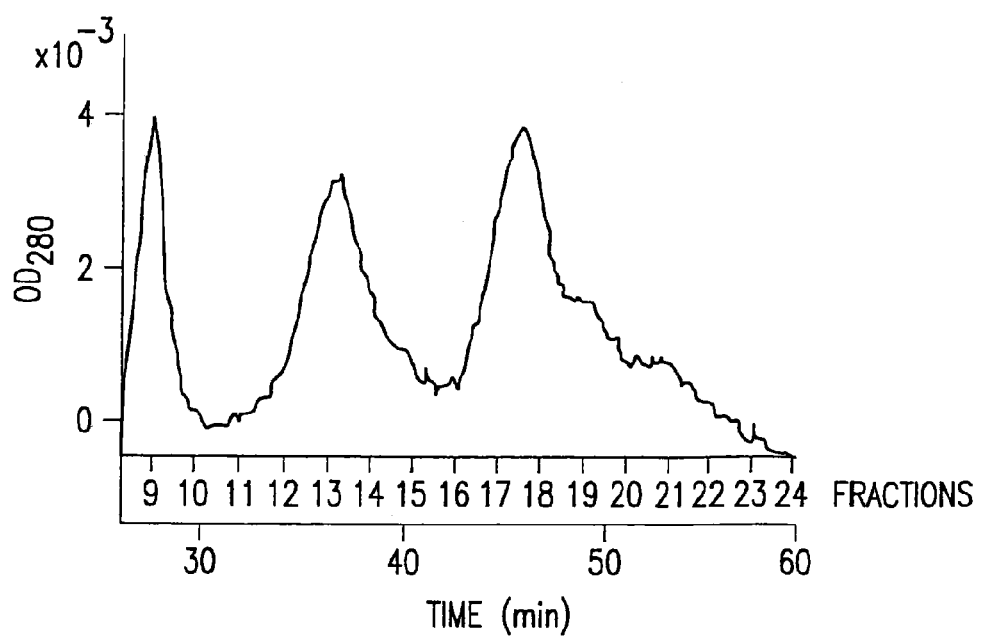
Figure 11B:
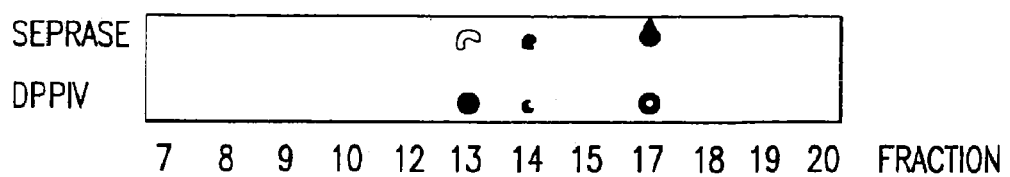

FIG. 11A-B. Gel Filtration Column Chromatography and Immunoblotting for Sepharase and DPPIV. FIG. 11A. WGA-purified, detergent-soluble proteins derived from WI38 cells were separated by a gel filtration column of Sepharase 12 (Pharmacal-LKB, Piscataway, N.J.). Protein standards used to calibrate the column were vitamin B-12 (1.35-kDa), myoglobin (17-kDa), ovalbumin (44-kDa), gamma globulin (158-kDa), catalase (232-kDa), ferritin (440-kDa), and thyroglobulin (670-kDa). FIG. 11B. Fractions were analyzed by immuno-dot blotting using mAbs against seprase and DPPIV. Seprase and DPPIV were found in 200-kDa (Fraction 17), 440-kDa (Fraction 14), and 670-kDa (Fraction 13) ranges, suggesting the presence of the seprase-DPPIV complex at 440-670 kDa sizes.

FIG. 12A-D. Characterization of the Seprase-DPPIV Complex Derived from WI38 Human Embryonic Lung Fibroblasts. FIG. 12A. Immunoprecipitation (Ip) of surface-biotinylated WI38 fibroblasts. Both mAbs; against seprase (D28) and DPPIV (E19) identified a RIPA-solubilized protein complex that contains two major bands at 170- and 200-kDa, indicative of seprase and DPPIV, respectively. FIG. 12B. The seprase-DPPIV complex demonstrated by Ip and immunoblotting (Ib). Seprase- or DPPIV-immunoprecipitates isolated from WI38 RIPA lysates were confirmed in seprase- or DPPIV-immunoblots but not in β1 or β3 integrin blots, suggesting that the protease complex is not associated with β1 and β3 integrins in RIPA. FIG. 12C. Gelatinolytic activity of the seprase-DPPIV complex. The protease complexes were analyzed by gelatin zymography in the absence of $Ca^{++}$ and in the presence of 2 mM EDTA. Both seprase and DPPIV immuno-isolates (Ip) exhibit a 170-kDa gelatinase (seprase) activity. FIG. 12D. DPPIV proline-specific peptidase activity of the complex. Both seprase and DPPIV immuno-isolates (Ip) exhibit same peptidase activity using fluorescent Ala-Pro-AFC (7-Amino-4-Trifluoromethyl Coumarin) substrate overlay assay. No activity could be observed for αv, α2, α6 or β3 integrin or control immuno-isolates.

Figure 13B:
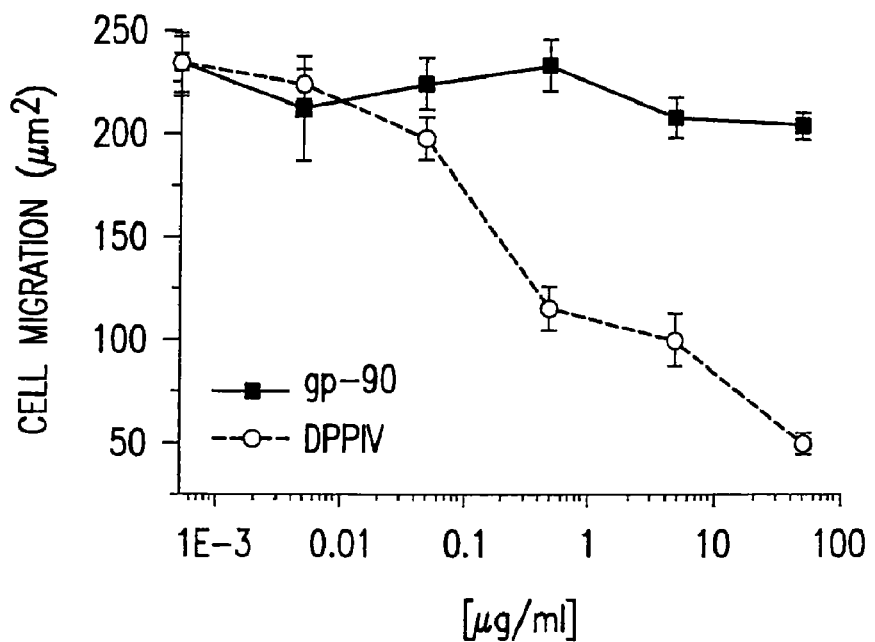
Figure 13C:
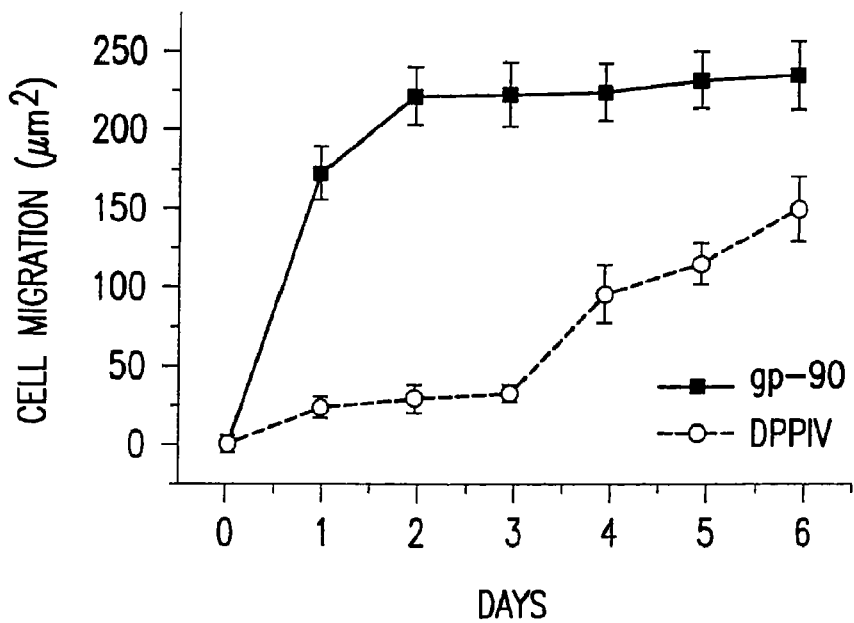
Figure 13D:
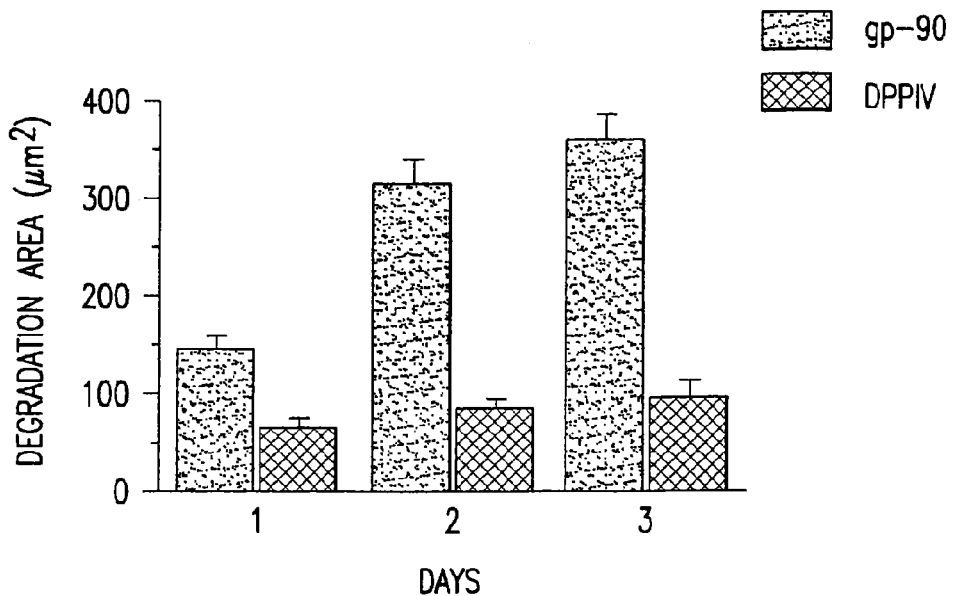
Figure 13E:
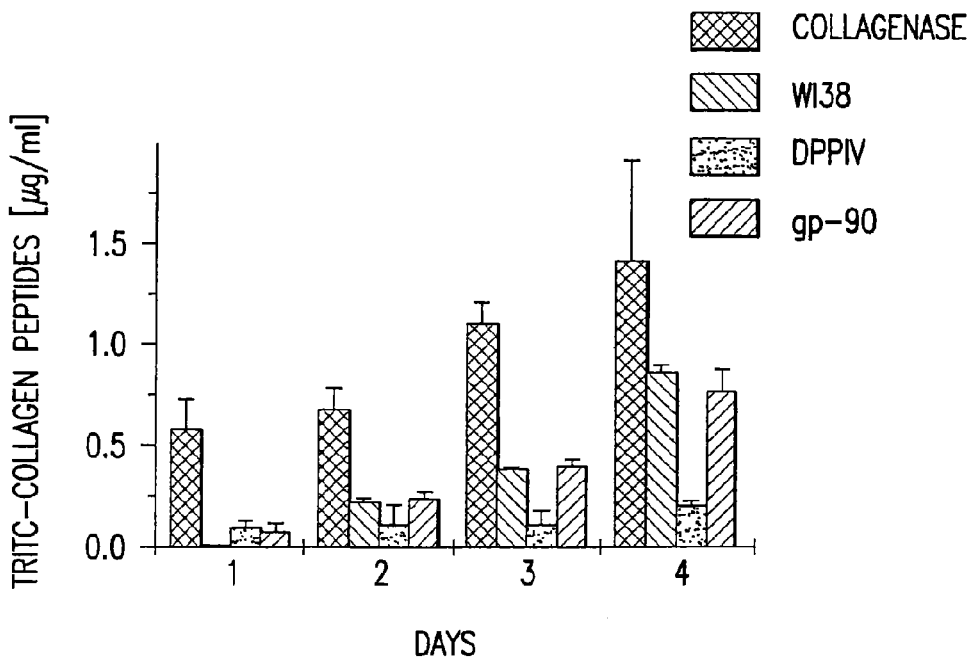

FIG. 13A-E. Cell Migration in Collagen Gel and Collagen Degradation by Wound-Activated WI38 Fibroblasts. FIG. 13A. Morphology of WI38 at 1 h (a, b, c) and 18 h (d, e, f) after wounding of the cell monolayer (photographed while cells were alive). Panel a & d: phase contrast of WI38 at the interface between the wound edge and cell-free glass surface, showing that spindle-shaped cells migrated on collagen fibers at 18 h (d). Panel b & e: fluorescent collagen gels in same fields shown in panels a & d. Uniform layer of TRITC-labeled collagen is seen at 1 h (b) but local removal of fluorescent collagen occurred at the wound edge by activated migrating cells at 18 h (e). Panels c & f: microscopic superimposed image of left and middle panels. Bar=10 μm. FIG. 13B. Dose-dependent inhibition of cell migration by inhibitory mAb E19 (against DPPIV) but not by control mAb C37 (against a cell surface glycoprotein gp-90). Three experiments of 24 h monolayer wound models were used for each antibody. Cell migration was quantified by measuring the areas of cell advancement from the original wound edge. The values are mean±SD. FIG. 13C. Reversal of antibody inhibition of cell migration. All antibodies, mAb E19 (against DPPIV) and mAb C37 (against gp-90), were applied at 5 μg per ml. After day 3, antibodies were removed and the antibody inhibitory effect was reversed. FIG. 13D. Histograms of the local removal of fluorescent collagen gel by wound-activated cells. Collagen degradation was measured as areas of fluorescent collagen removal by migratory cells. mAb E19 (against DPPIV) inhibited collagen removal by migratory cells while control mAb C37 (anti-gp-90) did not. All antibodies were applied at 5 g per ml. Three experiments were used for each antibody. The values are mean±SD. FIG. 13E. Collagen degradation by migratory cells in a sparse culture. Collagen degradation was measured by the release of fluorescent collagen peptides from a collagen gel by migratory WI38 cells. Bacterial collagenase was used as a positive control for fluorescent peptide release. All antibodies were applied at 5 μg per ml. Three experiments were used for each antibody. The values are mean±SD.

Figure 14A:
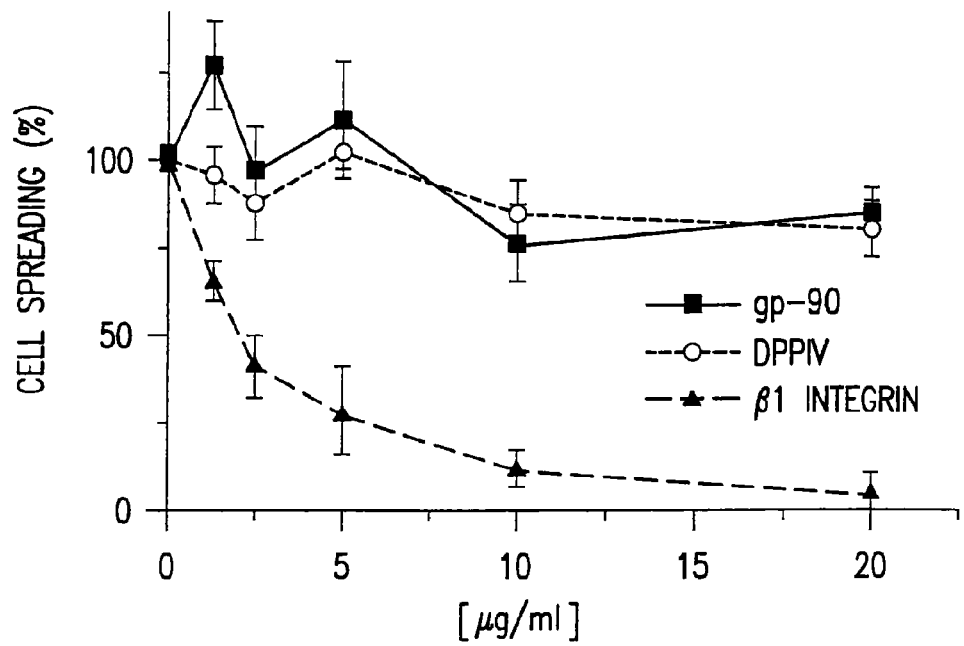
Figure 14B:
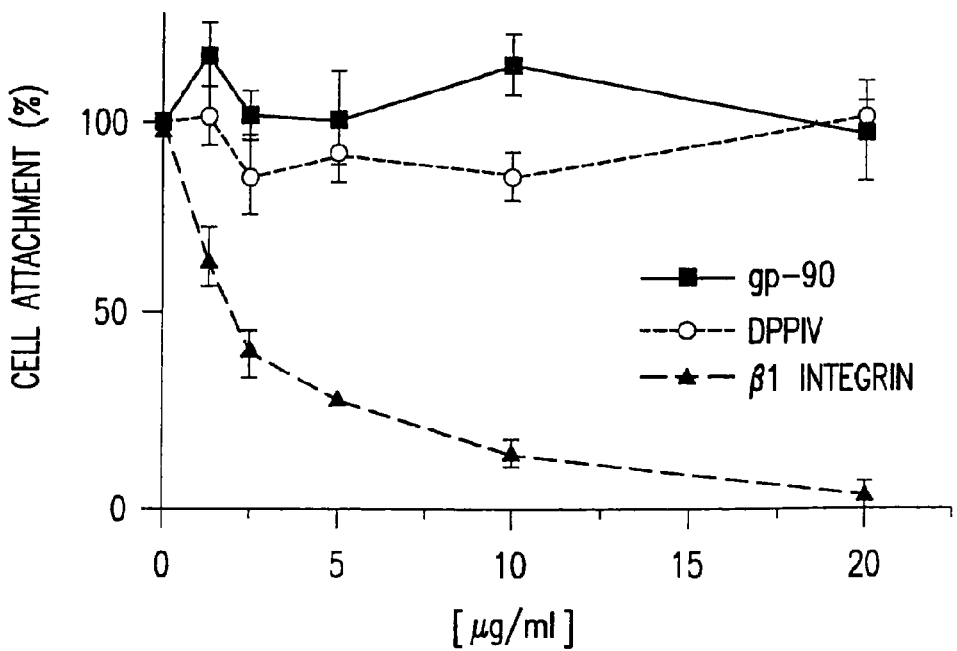
Figure 15A:
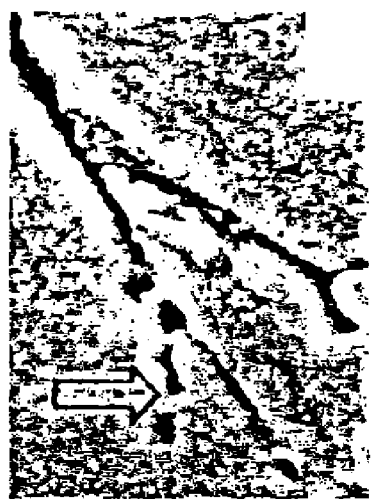
Figure 15B:
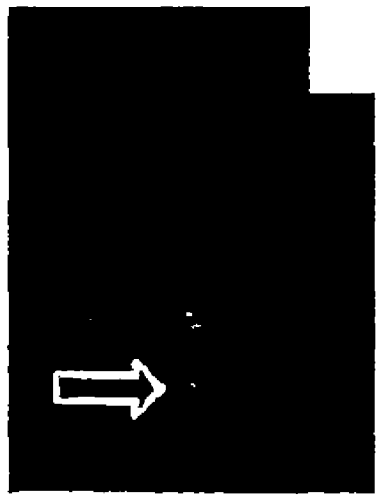
Figure 15C:
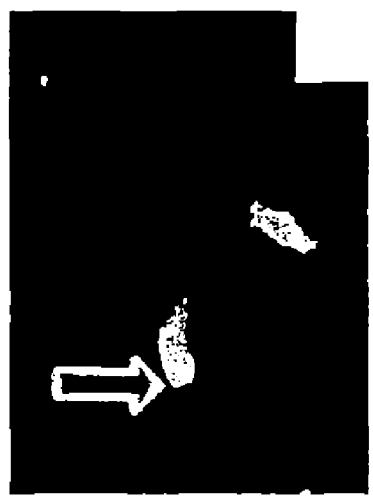
Figure 15D:
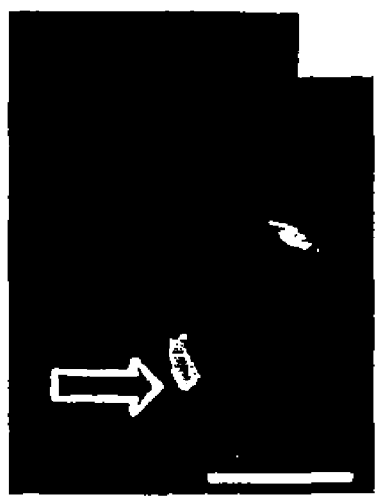

FIG. 14A-B. Attachment and Spreading of WI38 Cells on Collagen Substratum are Mediated Primarily by β1 Integrins but Not by DPPIV. FIG. 14A. Inhibition of WI38 cell spreading on collagen substratum by mAb C27 (against β1 integrins) but not by mAb E19 (against DPPIV) or mAb C37 (anti-gp-90). FIG. 14B. Inhibition of WI38 cell attachment to collagen substratum by mAb C27 (against β1 integrins) but not by mAb E19 (against DPPIV) or mAb C37 (anti-gp-90). Each value represents the mean of three separate determinations ±S.D. Duplicate experiments gave similar results.

FIG. 15. Co-localization of Seprase and DPPIV at Invadopodia of WI38 Cells Migrating in Collagen Gels. Phase contrast image of invadopodia (indicated by open arrow) in a WI38 cell migrating in type I collagen gel (a). Immunofluorescent image of DPPIV in the invadopodia (indicated by open arrow) that was labeled directly with TRITC-mAb E19 against DPPIV (b). Immuno-fluorescence image of seprase in the invadopodia (indicated by open arrow) that was labeled directly with FITC-mAb D28 against seprase (c). Superimposed image of panels b and c, showing that seprase and DPPIV co-localized at the invadopodia (indicated by open arrow) of a WI38 fibroblast migrating in collagen gel (d). Bar=10 µm.

Figure 16:
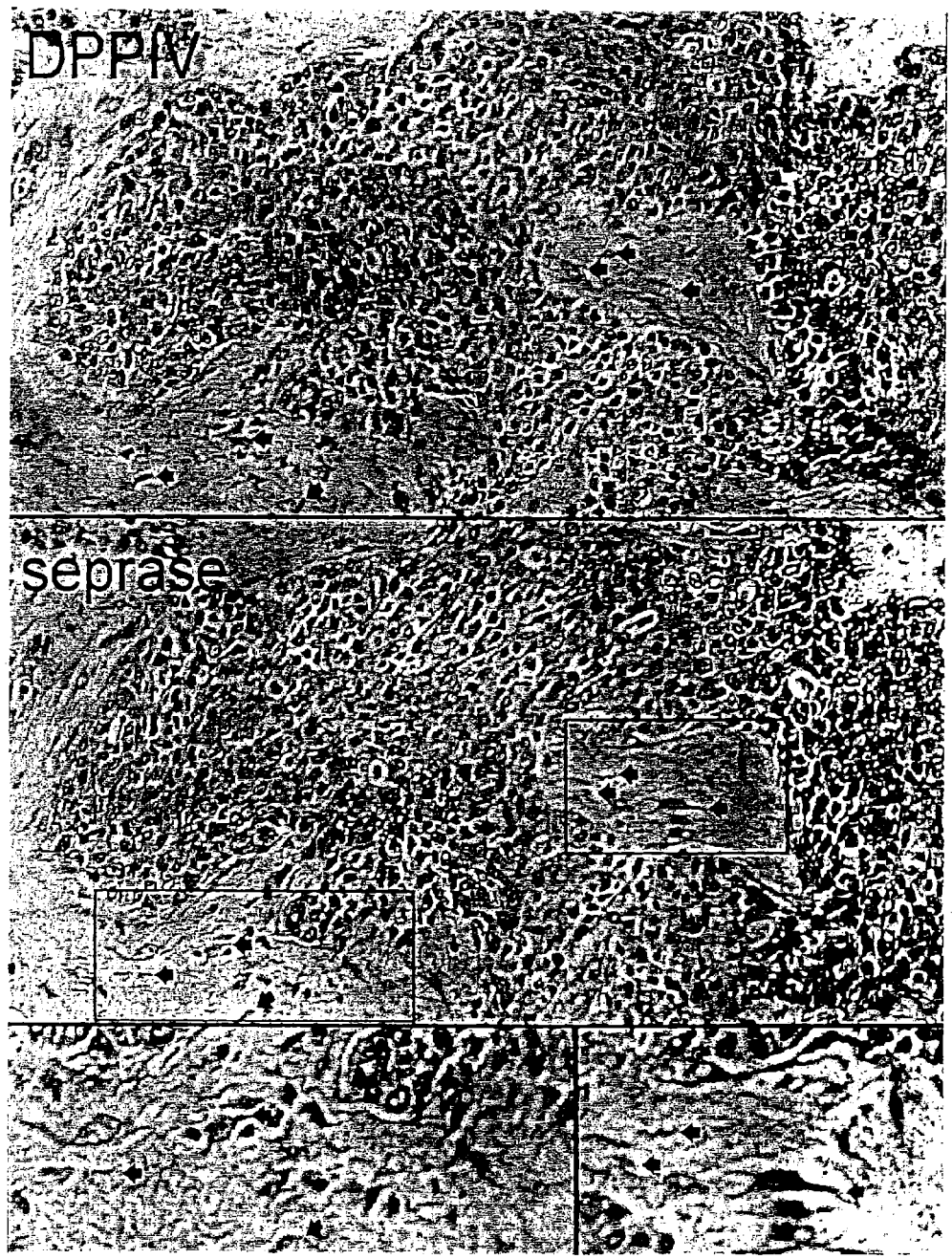
Figure 17A:
Figure 17B:
Figure 17C:
Figure 17D:
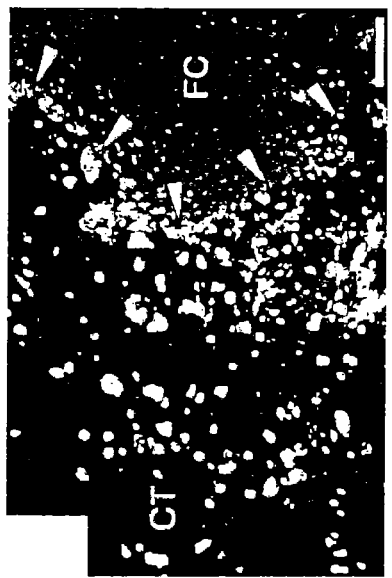
Figure 17F:
Figure 17H:
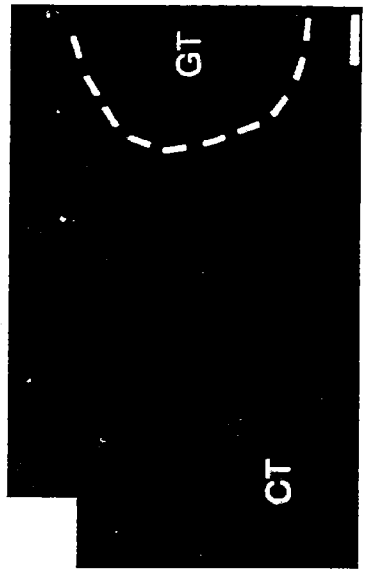
Figure 17E:
Figure 17G:
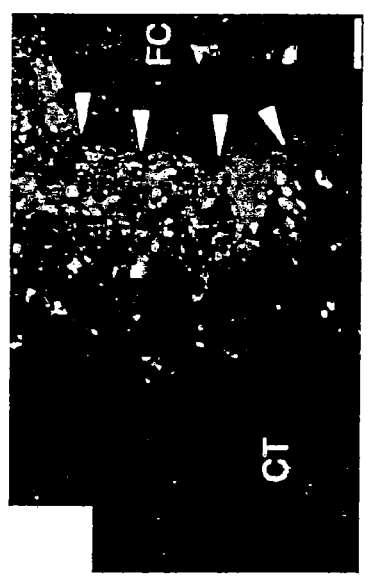
Figure 18A:
Figure 18B:
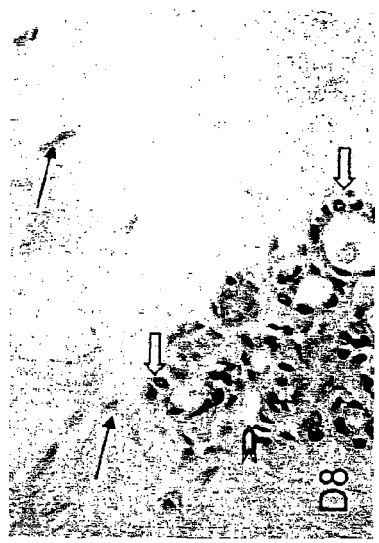
Figure 18C:
Figure 18D:
Figure 18F:
Figure 18E:

FIG. 16. Seprase and DPPIV Distribution in Connective Tissue Cells of Human Malignant Breast Carcinoma as demonstrated by immunohistochemistry of serial sections of paraffin-embedded tumor tissue. Both seprase and DPPIV are present in fibroblast-like cells of connective tissue immediately adjacent to invasive breast carcinoma but not in that of distant normal tissues (not shown). Arrows indicate positive brown, seprase or DPPIV stains for fibroblasts. Clusters of carcinoma cells are also positive for seprase (large cell aggregate in middle and bottom panels) and for DPPIV (large cell aggregate in top panel). Paraffin sections of breast carcinoma and adjacent normal tissue were placed in the same slide and stained with mAb D8 against seprase (middle and bottom panels) or mAb E26 against DPPIV (top panel). Bar=100 µm.

FIG. 17. Distribution of Seprase and DPPIV in Mucosa Cells of Healing Human Gingival Wounds. Frozen sections of healing mucosa wounds at 3-day-old (a, b, c, d and g) and at 7-day-old (e, f and h) were stained with hematoxylin and eosin (a and e), with TRITC-mAb D28 against seprase (b-d, and f) or with mAb E19 against DPPIV followed by TRITC anti-rat secondary antibody (g and h). In 3-day-old wound (a-d, and g), connective tissue (CT) contained cells that were strongly stained with seprase (b, c, and d) and DPPIV (g) antibodies. A confocal microscope image shows seprase localization at invadopodia in the form of filopodia (arrows) and cell bodies of fibroblast-like cells in connective tissue (panel d). In 7-day-old wounds (e, f and h), seprase staining was found (f) in the wound granulation tissue (GT), while DPPIV did not (h). Dotted lines indicate the border between granulation and connective tissues. Letter E indicates wound epithelium; CT, connective tissue; FC, fibrin clot; and GT, granulation tissue. Bar=200 µm.

FIG. 18. Co-localization of seprase and DPPIV in microvessel endothelial cells, fibroblasts, and carcinoma cells at the invasion front of human malignant breast ductal carcinoma. Formaldehyde-fixed, paraffin embedded malignant human breast ductal carcinoma samples were made in serial sections, seprase distribution was shown by brown staining using mAb D8 (left three panels) and DPPIV distribution on an adjacent section using mAb E26 (right three panels). Top two panels show normal breast tissues approximately 2 cm distance from tumor sites. Negative seprase and DPPIV stains were found in epithelial cells (black open arrows), fibrocytes (black arrows) and endothelial cells (black open arrowheads). Middle two panels indicate infiltrating sheets of poorly differentiated (high-grade) carcinoma cells with predominant brown cellular stains of seprase and DPPIV in tumor cells (orange open arrows), in fibroblasts (orange arrows), and in some endothelial cells (orange open arrowheads) but not in some larger vessel lining cells (black open arrows). Arrows in top and middle panels indicate a scale of 100 µm. Bottom two panels show low-magnification view of infiltrating sheets of poorly differentiated (high-grade) tumor cells with predominant brown cellular stains of seprase and DPPIV in tumor cells (orange open arrows), in fibroblasts (orange arrows), and in some endothelial cells (orange open arrowheads). Seprase and DPPIV are specifically expressed in tumor cells at the invasion front as indicated by most tumor cells in the field but are absent in these in the center of tumors as indicated in the center of the field. Arrows in bottom panels indicate a scale of 800 µm.

FIG. 19. Relationship of protease expression and collagen-degrading ability of MDA-MB-436 cells. A, Release of fluorescent collagen peptides by MDA-MB-436 cells differentially expressing seprase and DPPIV. Collagen degradation was measured by the release of fluorescent collagen peptides by parental cells (Parent), cells transfected with vector (pA11), cells transfected with seprase cDNA (pA15) and cells transfected with DPPIV ribozyme (pZ8). Three experiments were used for each and the values were mean±SD. Star "*" indicates ($p<0.05$ for pA15 seprase sense and pZ8 DPPIV ribozyme transfectants as compared to parent and pA11 vector transfected cells. B, Differential expression of seprase and DPPIV in above-mentioned MDA-MB-436 cells. Cells were extracted with RIPA buffer and immunoblots were done using mAb D8 (Anti-seprase) and mAb F4 (Anti-DPPIV).

5. DETAILED DESCRIPTION THE INVENTION

The present invention relates to a novel method for forming a cell-adhesion matrix for isolation and detection of a subpopulation of cancer cells which are viable, invasive, and metastatic from a sample derived from a subject possessing a cancer. In particular, a method is described that utilizes a collagenous matrix system for isolation and detection of cancer cells. The invention described in the subsections below further relates to a novel highly sensitive in vitro assay for measuring the metastatic potential of a cancer. An important feature of the assay includes applicability to cancer cells in blood, bone marrow, ascites, body fluid, and tumor tissue, or any established cancer cell line.

The "cell-adhesion matrix" of the invention provides a cancer cell trap that allows for the high yield and efficient removal of viable cancer cells from whole blood, buffy coat, peripheral blood stem cell preparation or bone marrow. The cell separation method of the present invention may be used for cancer diagnostic purposes, e.g. early detection, monitoring therapeutic and surgical responses, and prognostication of cancer progression. The cell separation method of the present invention may also be used for cancer preventive and therapeutic purposes, including the use in blood filter as a cancer cell trap, in genetic and cytogenetic analyses, in new drug target discovery, and in cancer vaccine development.

The in vitro assay system of the invention further provides a screening method for identifying agents with anti-metastatic activity. Such agents may be used to inhibit metastatic spread of cancer cells in subjects having cancer. In addition, the assay may be used to screen for nucleic acid molecules with anti-metastatic potential. For example, antisense and ribozyme molecules may be screened for their ability to inhibit metastasis. In yet another embodiment of the invention, the activity of seprase or DPPIV may be measured to determine the metastatic potential of cancer cells.

5.1 The Matrices of the Invention

The present invention provides a novel, natural, cell-adhesion matrix system that may be used for the isolation and detection of cancer cells from samples derived from cancer subjects. The natural cell-adhesion matrix of the invention has specific binding affinity for blood-borne cell adhesion components, including but not limited to fibronectin, laminin and vitronectin. The present invention is based on the observation that cancer cells present in the circulation of patients with metastatic diseases can attach to tissue fragments and form large cellular clusters indicating that natural structural scaffolds have a high affinity for blood-borne adhesion molecules and, therefore, promote attachment of metastasized cancer cells. Additionally, it was discovered that natural fibers, including type I/III collagen, fibrin, purified cotton, and mechanically scratched surfaces of tissue culture plastic, absorb preferentially blood-borne adhesion components that promote adhesion of cancer cells.

The present invention encompasses cell-adhesion matrices comprising collagenous fibers, fibrin gels, purified cotton or plastic fibers for use as a cellular substratum for the detection and isolation of viable human cells in vivo, these cells include but not limited to carcinoma, endothelial and tissue cells. A variety of commercially available collagenous materials may be used to prepare the collagen matrix, including, but not limited to, human placental type I collagen, purchased from Calbiochem-Novabiochem Co. (La Jolla, Calif.); and rat-tail type I collagen, available from Collaborative Biomedical Products (Becton and Dickinson Labware, Bedford, Mass.). Any form of recombinant collagen may also be employed, as may be obtained from a collagen expressing recombinant host cell, including bacterial, yeast or mammalian cells.

Type I collagen can be readily assembled and reassembled into any form and be coated on vessel surfaces through cycles of polymerization and de-polymerization. For example, it is well-known that type I collagen monomers, at a concentration of over 0.3 mg/ml, polymerize under conditions of natural pH, warm temperatures (25-37° C.) and medium containing saline, and that collagen fibers de-polymerize in the condition of pH 2-4, cold temperatures (2-10° C.), and low salt medium (Klasson, S. C., et al. 1986, Coll. Relat. Res. 6:397). Such a cell-adhesion matrix can be formed lining the wall of a micro capillary, cell isolation columns, tissue culture plates, or micromesh for capture of cancer cells in biological fluids.

The matrix scaffold of the present invention may be composed of natural fibers, including, but not limited to, collagens, fibrin and purified cotton. A common property of these matrix scaffolds is that their surfaces have affinity for blood-borne adhesion molecules, including, but not limited to, fibronectin, vitronectin and laminin. The matrix scaffold, when coated with cell adhesion molecules present in whole blood, plasma or serum, provides an adhesive surface which supports the attachment of cancer cells and tissue cells from high-density cell populations. These populations may be derived from blood, lymph, bone marrow and tumor tissue and may include many different cell types.

The method of preparing a collagenous matrix is described in detail in this application. A matrix scaffold composed of fibrin fibers were prepared on vessel's surfaces by reducing the anti-coagulant content of plasma. Animal or human plasmas were initially diluted to 10-20% with Dulbecco's modified Eagle's medium (DMEM) and added into cell isolation vessels or wells. The vessels or wells were incubated for 30 min at 37° C. in a $CO_2$ incubator to allow polymerization of the fibrin fibers on vessel's surface. Purified cotton fibers were simply suspended in DMEM containing 10-20% bovine serum and seeded in cell culture wells for coating of cell adhesion molecules. Similarly, glass and plastic fibers were coated with cell adhesion molecules by suspension in DMEM containing 10-20% bovine serum. A cell culture plate was scrapped with an Eppendorf peptide tip to prepare as a matrix scaffold. It should be noted that pre-coating of cell adhesion molecules to a matrix scaffold is not necessary when whole blood or a buffy coat will be applied to a matrix scaffold. However, whole blood or buffy coat should be treated with anticoagulants to prevent coagulation during the cell separation procedure. Specifically, blood or buffy coat were pre-diluted with equal volume of medium containing 0.5 mM EDTA or with 10% anticoagulant citrate dextrose (ACD; Baxter Healthcare Corporation, IL) containing 50 unit heparin/ml.

To facilitate detection of cancer cells bound to the collagenous matrix and to measure the metastatic potential of such cells, the matrix can be labeled with a variety of different agents, including, but not limited to, fluorescent dyes, biotin, color dyes, and radioactive probes. For example, collagen fibers can be labeling by direct conjugation of dyes thereby protecting polymerization sites in the collagen from labeling. Collagen fibers, either labeled by this method or unlabeled, can be readily disassembled into soluble collagen monomers, which can be subsequently assembled into any form on vessel surfaces. Preferred dyes for labeling of collagen include Bodipy-rhodamine or fluorescein dyes, available from Molecular Probes, Inc., which are quench-fluorescent dyes. As illustrated in FIGS. 1A and 1B, Bodipy-rhodamine's fluorescent signal (yellow) is reduced when two dye molecules are situated close together on collagen but is increased (red) when collagen is degraded or cleaved by enzymes to separate two dye molecules. Methods for labeling of the matrix are well known to those of skill in the art. Likewise, conjugation of a cytotoxic compound to such collagen fiber can provide a novel vehicle for delivery of the drug to specific cancer cells. For example, injection of a cytotoxin-conjugated, collagen microsphere into a patient with cancer can achieve specific killing of cancer cells.

The surface of a matrix scaffold is further coated with blood-borne adhesion molecules. A variety of commercially available solutions containing blood-borne adhesion molecules can be used to coat the matrix, including, but not limited to, calf serum, fetal calf serum (Collaborative Research, Inc., Bedford, Mass.); human serum (Sigma); and human plasma fibronectin, laminin and vitronectin (Collaborative Research, Inc., Bedford, Mass.). The surface of the matrix scaffold can be coated with adhesion molecules using either 10-20% of calf serum, fetal calf serum, or human serum (or plasma), or 0.01-0.5 milligram per milliliter of human plasma fibronectin, laminin and vitronectin.

The present invention achieves a highly desirable objective, namely providing a method for prevention and intervention of metastases formation in a cancer subject by a cell separation system. Specifically, the invention encompasses a method for isolation of cancer cells derived from a cancer subject comprising:

(a) inoculating a cancer cell sample derived from a cancer subject onto cell-adhesion matrix;

(b) incubation of the cancer cell sample for a time sufficient to allow adhesion of cancer cells to the matrix, followed by removal of non-adherent cells; and (c) ex vivo propagation of cancer cells bound to the matrix.

The cell separation method of the present invention may be used to isolate any desired cancer cell population from in vivo or in vitro sources including, but not limited to, body fluids, e.g. circulating blood, urine, bone marrow, spinal and pleural fluids, ascites, sputum; dissociated tumor tissue specimens; and cultured tumor cells. Examples of desired cancer cell populations include, but are not limited to, carcinoma cells of prostate, breast, colon, brain, lung, head & neck, ovarian, bladder, renal & testis, melanoma, lymphoma, liver, pancreatic and other gastrointestinal cancer. Specifically, desired cancer cell population from various cancers include lung carcinoma cells, lung adenoma cells, colon adenocarcinoma cells, renal carcinoma cells, rectum adenocarcinoma cells, ileocecal adenocarcinoma cells, gastric adenocarcinoma, pancreatic carcinoma, hepatoma cells, hepatocellular carcinoma cells, prostate adenocarcinoma cells, bladder carcinoma cells, breast carcinoma, ovarian teratocarcinoma, amalanotic melanoma cells, malignant melanoma cells, squamous cell carcinoma of the cervix, larynx and of oral origin; glioblastoma cells, endometrial adenocarcinoma, astrocytoma, Burkitt lymphoma cells, and non Hodgkin's lymphoma cells.

The presence of cancer cells bound to the matrix can be detected using a variety of different methods including the use of functional, immunophenotypic and cytomorphologic features of neoplastic cells. Additionally, any bound cell may be detected based on the ingestion of the labeled collagenous matrix by the cells.

5.2 Therapeutic and Preventive Applications in the Present Invention

The present invention provides cell separation methods that may be used, for example, to remove undesired cancer cells and to enrich hematopoietic progenitor cells from the blood or bone marrow for use as donor cells in bone marrow transplantation. Following cell separation methods, antibodies reactive with carcinoma epitopes such as epithelial markers, or antibodies reactive with endothelial cells, such as anti-CD31 or anti-CD34, can be used to enrich for cancer or endothelial cell populations, respectively.

In a specific embodiment, cancer cells derived from different cancers may be enriched from whole human blood by the cell separation methods of the present invention, subjected to ex vivo expansion, then used to interact with dendritic cells to develop an effective tumor vaccine using procedures including a method described (Brugger et al., 1999, Annals of the New York Academy of Science 872:363-371).

In another embodiment of the invention, circulating cancer cells can be isolated from a cancer subject and then subjected to a battery of chemotherapeutic regimes in vitro to determine the efficacy of a specific treatment. Effective doses or drug combinations could then be administered to that same subject (designer drugs).

In another embodiment of the invention, a cytotoxin-conjugated collagen microsphere can be injected into a patient with metastatic cancer for selective killing of cancer cells. Specific adhesion and internalization of toxic collagen by cancer cells in vivo may provide a novel treatment.

The invention also provides fibrous compositions, including but not limited to blood-borne adhesion molecule-coated collagen, fibrin, cotton and plastic fibers, to be used as cell-adhesion matrices for use as blood filters by subjects having metastatic cancer. The use of such a cell-adhesion matrix involves the perfusion of the subject's blood through the cell-adhesion matrix. In the blood perfusion protocol, the subject's blood is withdrawn and passes into contact with the cell-adhesion matrix. During such passage, cancer cells present in the patient's blood, preferentially adhere to the cell-adhesion matrix and are removed from the circulation of the patient.

To form the cell-adhesion matrix, collagen or the above-mentioned material is formed within a vessel, including but not limited to columns, tissue culture plates, microcapillaries, or micromesh for capture of cancer cells in biological fluids. The vessel contains an input and output outlet for passage of the subject's blood through the containment vessel. In a specific embodiment of the invention, the cell-adhesion matrix may be formed within a containment vessel which includes a blood input line, which is operatively coupled to a conventional peristaltic pump. A blood output line is also included. Input and output lines are connected to appropriate arterial venous fistulas, which are implanted into, for example, the forearm of a subject. Alternatively, apheresed peripheral blood can be applied in conjunction with the above-mentioned cancer cell isolation by the cell-adhesion matrix. Apheresis was initiated upon recovery of the white blood cell count to equal or more than $1.\times 10.^9/L$. Apheresis or leukopheresis can be performed using a Cobe Spectra Cell Separator (Lakewood, Colo.) at a rate of 80 ml/min for 200 min (total volume of 16 L). The use of the cell-adhesion matrix of the invention provides a novel method that can remove cancer cells from the circulation of a patient in which cancer cells have great potential to metastasize.

5.3 Assays for Measuring Metastatic Potential of Cancer Cells

It is an object of the present invention to provide a method for the identification of subjects possessing a cancer with an increased metastatic potential. The present invention relates to evaluation of metastatic potential by detecting the ability of a subject's cancer cells to invade, i.e., adhere, degrade and ingest a collagenous matrix, using the collagen based cell-adhesion matrix system of the present invention. The detection and measurement of the cancer cell's angiogenic propensity, cell viability and proliferation constitute additional novel strategies for prognosis of cancer.

The cell separation and assay methods described herein may be used for a variety of diagnostic uses. These uses include morphological, molecular, biochemical or immunological assays in early detection, in monitoring therapeutic and surgical response, and in prognostication of cancer progression. For example, RNA may be prepared from circulating cancer cells and subjected to real-time polymerase chain reaction (PCR), DNA microarray analysis and serial analysis of gene expression (SAGE) and to identify differentially expressed genes that are diagnostic markers for cancer or drug targets for controlling metastasis. Furthermore, protein profile of isolated cancer cells can be done by proteomics analyses to discover novel metastatic markers and drug targets. The isolated cancer cells may be stained for epithelial specific antigens, seprase and DPPIV antigens or endothelial cell markers, and quantitated to determine the number of cancer cells present for evaluating the metastatic potential of a cancer. The isolated cancer cells may be assessed morphologically as a routine pathological evaluation of a cancer. The isolated cancer cells may be cultured under sterile conditions and subjected to cytogenetic analysis to detect the presence of chromosomal abnormalities and mutation determination. The isolated cancer cells may be reacted with molecular probes for more sensitive detection of mutation using DNA microarray, PCR and FISH. The methods thereby avoid the use of invasive and expensive surgical procedures heretofore relied upon for such a determination.

The present invention achieves a highly desirable objective, namely providing a method for the prognostic evaluation of subjects with cancer and the identification of subjects exhibiting a predisposition to developing metastatic cancer. Specifically, the invention encompasses functional assays for determining the metastatic potential of cancer cells isolated from a subject using the cell-adhesion matrices of the present invention.

Specifically, the invention encompasses a method for determining the metastatic potential of cancer cells derived from a cancer subject comprising:
(a) inoculating a cancer cell sample derived from a cancer subject onto a cell-adhesion matrix;

(b) incubation of the cancer cell sample for a time sufficient to allow adhesion to, migration across or ingestion of the matrix by the cancer cells to occur; and (c) detection of adhesion to, migration across or ingestion of the material by the cancer cells wherein detection of cancer cell adhesion to, migration across or ingestion of the material is an indicator of cancer cells with metastatic potential.

The assay of the invention involves the creation of an artificially generated matrix onto which cancer cells are inoculated. Cells which may be inoculated onto the matrix include but are not limited to blood cells, cancer cell lines and cells derived from the tumor of a mammal, including cells derived from the tumor of a cancer subject, i.e., biopsied tumor tissue, etc.

Once the cancer cells have been inoculated onto the matrix, the matrix is incubated for a time sufficient to allow adhesion, ingestion or invasion to occur. The inoculation time will vary depending on the metastatic potential of the inoculated cancer cells.

Following incubation, cancer cell adhesion to the matrix and/or ingestion of the matrix by cancer cells is detected using a variety of different methods. For example, a collagenous matrix may be labeled with agents such as, for example, fluorescent dyes, biotin, color dyes and radioactive probes. Ingestion of the matrix by the cancer cells results in labeling of the cells. The detection of cancer cells expressing the labeled markers may be accomplished using a variety of different methods well known to those skilled in the art including but not limited to fluorescence microscopy, fluorescent activated cell sorting (FACS) or scintillation counter measurement of radioactivity. Using such labels, the level of cell adhesion and ingestion of matrix material may be quantitated to determine the metastatic potential of the cells.

In addition, the metastatic potential of cancer cells isolated using the matrices of the invention may be determined using a variety of different assays well known to those skilled in the art. For example, the cancer cell sample can be incubated with labeled acetylated low density lipoprotein (acLDL+), plated on a collagen gel for capillary network formation, or stained with antibodies directed against endothelial cell markers, including but not limited to CD31+, Flk1+, and factor VIII (F8+) for a time sufficient to allow measurement of the acquirement of the endothelial phenotype by cancer cells to occur. Alternatively, the propensity of the cancer cells to undergo apoptosis may be measured using an apoptosis assay kit (Molecular Probes, Inc.). The cancer cell clusters may be reacted with antibodies directed against leukocyte markers, including but not limited to CD45, CD19, CD8, and CD4 for a time sufficient to allow numeration of cancer cell viability, association with immune cells (leukocytes, T-cells and killer cells) and resistance to cellular or complement cytolyses. The ability of isolated cancer cells to form colonies in culture can also be determined by propagating the cancer cells in tissue culture medium containing 10-20% human plasma for 1-5 weeks thereby allowing the cancer cells to form clones.

The assay system of the invention can also be used to monitor the efficacy of potential anti-cancer agents during treatment. For example, the metastatic potential of cancer cells can be determined before and during treatment. The efficacy of the agent can be followed by comparing the number or metastatic potential of the cancer cells throughout the treatment. Agents exhibiting efficacy are those, which are capable of decreasing the level of detectable cancer cell adhesion, degradation or ingestion of a collagenous matrix, the cancer cell viability, and the colony-forming ability.

5.4 In Vitro Screening Assay for Identification of Anti-Metastatic Agents

The present invention further provides screening assays for identification of agents capable of inhibiting the spread of cancer cells from a primary tumor to a site of metastasis formation. In accordance with the invention, agents may be screened for their ability to inhibit metastasis of cancer cells. In utilization of the assay of the invention for purposes of identifying anti-metastatic agents, the test agent is co-inoculated with cancer cells onto the collagenous matrix. The adhesion, ingestion and/or degradation of the collagenous matrix by cancer cells in the presence of a test agent is compared to the adhesion, ingestion and/or degradation of the collagenous matrix in the presence of a vehicle control, wherein an anti-metastatic agent is identified as one capable of inhibiting the adhesion, ingestion and/or degradation of the collagenous matrix by cancer cells.

Specifically, the invention comprises a method for identifying an agent that inhibits metastasis of cancer cells comprising:

(a) inoculating a cancer cell sample and either a test agent or a vehicle control onto the cell-adhesion matrix (b) incubation of the matrix for a time sufficient for adhesion, degradation and/or ingestion of the matrix by the cancer cells to occur; and (c) detecting the adhesion and/or ingestion of the matrix by the cancer cells, wherein a decrease in the adhesion, ingestion and/or degradation of the collagenous matrix by the cancer cells in the presence of the test agent, as compared to the number of cancer cells detected in the presence of a vehicle control, identifies a compound that inhibits metastases formation.

The agents which may be screened in accordance with the invention include, but are not limited to inorganic compounds, peptides, antibodies and fragments thereof, and other organic compounds (e.g., peptidomimetics) that are capable of inhibiting the spread of cancer cells from a primary tumor to a site of metastases formation. Agents may include, but are not limited to, peptides such as, for example, soluble peptides, including but not limited to members of random peptide libraries; (see, e.g., Lam, K. S. et al., 1991, Nature 354:82-84; Houghten, R. et al., 1991, Nature 354:84-86), and combinatorial chemistry-derived molecular library made of D- and/or L-configuration amino acids, phosphopeptides (including, but not limited to, members of random or partially degenerate directed phosphopeptide libraries; see, e.g., Songyang, Z. et. al., 1993, Cell 72:767-778).

Agents identified via assays such as those described herein may be useful, for example, in defining the properties of cancer cells that enable successful migration and invasion, and for inhibiting metastases formation in cancer subjects. Assays for testing the efficacy of compounds identified in the screens can be tested in animal model systems for metastasis formation. Such animal models may be used as test substrates for the identification of drugs, pharmaceuticals, therapies and interventions which may be effective in treating cancer metastasis.

The assay of the invention may also be used to screen for nucleic acid sequences capable of inhibiting the metastatic potential of cancer cells. Such nucleic acid molecules include molecules comprising protein coding sequences or anti-sense sequences. The nucleic acid molecules may be transferred to cancer cells prior to assaying by such methods as electroporation, lipofection, calcium phosphate mediated transfection, or viral infection.

In accordance with the invention, an assay system can be used to screen for agents that modulate the activity of serine integral membrane proteases, including DPPIV and seprase and thereby modulate the metastatic potential of cancer cells. To this end, cells that endogenously express DPPIV and seprase can be used to screen for agents. Alternatively, cell lines, such as 293 cells, COS cells, CHO cells, fibroblasts and the like are genetically engineered to express DDPIV and seprase for use in screening. Preferably, host cells genetically engineered to express DDPIV and seprase can be used as an endpoint in the assay; e.g., as measured by a chemical, physiological, biological or phenotypic change.

In utilizing such cell systems, the cells expressing the DDPIV and seprase are exposed to a test compound or to a vehicle control. After exposure, the cells can be assayed to measure the expression and/or activity of DDPIV and seprase protease activity. For example, after exposure, cell lysates can be assayed for gelatinolytic activity (seprase), or substrates containing phosphorylated residues adjacent to proline, such as H-Gly-Pro-p-nitroanilide or amino methylcoumarin (DPPIV and seprase) and Z-Gly-Pro-p-nitroanilide or amino methylcoumarin (seprase) (Kaspari et al., 1996). The ability of a test compound to decrease levels of DPPIV and/or seprase protease activity, below those levels seen with cells treated with a vehicle control, indicates that the test compound inhibits DDPIV and seprase associated protease activity.

In addition, assays may be used to identify agents that antagonize the interaction between DPPIV and seprase, thereby inhibiting the activity of the protein complex. To identify such agents, DPPIV and seprase proteins are incubated in the presence and absence of a test compound followed by detection of complex formation. A decrease in complex formation indicates the identification of an agent capable of antagonizing the interaction between DPPIV and seprase.

In one aspect of the invention, soluble DPPIV and seprase may be recombinantly expressed, labeled and utilized in none-cell based assays to identify compounds that inhibit the interaction between DPPIV and seprase. In such assays, either the DPPIV or seprase can be attached to a solid substrate such as a test tube or microtitre well, by means well known to those known in the art. The test agents are then assayed for their ability to inhibit the interaction between DPPIV or seprase on the solid substrate.

5.5 Compositions and Uses

The present invention relates to a novel cancer cell capture system for rapid and efficient detection and selection of invasive cancer cells from the blood and/or tissue of cancer patients. The invention relates to fibrous compositions comprising blood-borne adhesion molecule-coated collagen, fibrin, cotton, and plastic fibers, to be used as cell-adhesion matrices. The invention further relates to use of such coated fibers to detect the presence of metastatic cells in cancer patients, and to filter the blood of subjects having metastatic cancers. Cell-adhesion matrices that may be administered to subjects with cancer include those described in Sections 5.1.-5.2., supra.

The present invention also provides cellular compositions that can be isolated by the cell-adhesion matrix of this invention. Such cellular compositions comprise a small subpopulation of tumor cells that have potential to metastasize, as well as cancer cell clusters in the blood that may contribute to organ dysfunction associated with late stage cancer. The enriched cancer cell population can be used, for example, to determine novel drug targets, genetic defects involved, their metastatic potential and the most effective treatment regime. The enriched cells may also be used in fusions with dendritic cells for cancer vaccine development.

The present invention provides for treatment of proliferative disorders such as cancer, by administration of agents that regulate the metastatic activity of cancer cells. Compounds that may be administered to subjects with cancer include those agents identified using the assays described in Sections 5.3., supra.

In a specific embodiment of the invention, key proteases required for the tissue invasive phenotype were identified. For example, activation of serine integral membrane proteases, such as seprase and DPPIV were shown to be required for tissue cell migration and invasion. Thus inhibitors of such proteases may be used to inhibit the metastatic activity of cancer cells. Such inhibitors include antibodies immunospecific for seprase or DPPIV (FIG. 13A-E). Alternatively, transfection into cancer cells of a vector expressing antisense RNA or ribozymes for seprase or DPPIV may be used to reduce the ability of cancer cells to metastasize (FIG. 19).

In addition, protease inhibitors may be administered to inhibit the spread of cancer cells from a primary tumor to a site of metastasis formation. As demonstrated in Section 7, Example 2, an inhibitor of DPPIV, i.e., an anti-DPPIV antibody, was capable of inhibiting cancer cell migration. Cancers involving metastasis of tumor cells to other locations in the body are treated by administration of an agent that inhibits cancer cell migration and tissue invasion. Such cancers include, for example, carcinomas, such as breast cancer and prostate cancer.

Compounds identified for use in prevention of cancer cell metastasises can be tested in suitable animal model systems prior to testing in humans, including but not limited to dogs, rats, mice, chicken, cows, monkeys, rabbits, etc. For in vivo testing, prior to administration to humans, any animal model system known in the art may be used.

In specific embodiments, compounds that inhibit cancer metastasis are administered to a subject having cancer where it has been determined that the subject's cancer cells have an increased metastatic potential. The increased metastatic potential can be readily detected, e.g., by obtaining blood sample (or biopsy tissue from a patient) and assaying for the metastatic potential of the isolated cancer cells using the cell separation and assay system of the present invention.

The invention provides methods of treatment of cancer by administration to a subject of an effective amount of a compound that inhibits the metastatic potential of cells. In a preferred aspect, the subject is an animal, and is preferably a mammal, and most preferably human.

The present invention also provides pharmaceutical compositions that can be linked to the cell-adhesion matrix or its isolated cellular component of this invention. Such compositions comprise a therapeutically effective amount of the compound capable of regulating the migration and invasion of cancer cells, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

6. EXAMPLE

Isolation of Circulating Carcinoma Cells Involved in Angiogenesis and Metastasis The data provided below, demonstrates that viable carcinoma cells can be isolated from peripheral blood of cancer patients with metastatic diseases by novel cell-adhesion matrix cell separation and assay methods, and these cells acquire molecular determinants necessary for angiogenesis and metastasis to occur. Comparing to the cells derived from primary tumor, such viable circulating cancer cells represent a small subset of cancer cell population that have potential to metastasize.

6.1 Materials and Methods

6.1.1 Collection of Blood Sample

Blood or cells collected from an in vivo source are subjected to cell isolation within a relatively short time after their collection because the cells may lose their viability. In order to maintain the optimal isolation of cancer cells, it is preferred that blood, ascites or tissue samples are stored at 4° C. and used within 24 hours after their collection, most preferably, within four hours. Approximately 10-20 ml of blood each time were collected in Vacutainer tubes (Becton Dickinson, green top, each tube holds 7-ml) containing Lithium Heparin as anticoagulant. Patient age, sex, date of diagnosis, therapeutic interventions, clinical status, and biopsy report were retrieved from the patients' charts. The protocol was approved by the institutional review boards.

6.1.2 Isolation of Cancer Cells from Blood or Tumor Tissue

The collagen polymerization solution was prepared and adjusted to a pre-determined concentration, from 1 to 2 milligrams per milliliter for collagens in Dulbecco's modified Eagle's medium (DMEM), on ice immediately prior to the gelation into vessel substrata (FIG. 1A). Specifically, type I collagen solution (rat-tail type I collagen, 4.0 mg/ml, Collaborative Biomedical Products, Becton and Dickinson Labware, Bedford, Mass.) was mixed with equal volume of DMEM at 4° C. The mixture was overlaid as a thin layer onto the bottom of 96-well microtiter or 6-well culture plates (Nunc, Inc., Naperville, Ill.) at 4° C. To form a gel of collagen fibers, plates were incubated for 30 minutes at 37° C. to allow polymerization of collagen layer.

6.1.3 Isolation of Cancer Cells from Blood, Ascites or Tumor Tissue

To separate cancer cells from a cell population, the collagen matrix was first coated with the cell culture medium, consisting of a 1:1 mixture of Dulbecco's modified Eagle's medium (DMEM) and RPMI1640 supplemented with 10% calf serum, 15% Nu-serum (Collaborative Research, Inc., Bedford, Mass.), 2 mM L-glutamine, 0.1 mM non-essential amino acids, 1 mM sodium pyruvate, 1 unit/ml penicillin, and 10 μg/ml streptomycin. However, cancer cells can be isolated directly from whole blood without the need to coat additional adhesion molecules, which are present in the blood.

The samples were processed for plasma and cell isolation at 4° C. Blood samples were centrifuged to collect plasma, and cell pellets were diluted with PBS containing 2% bovine serum and 0.5 mM EDTA to the original volume and then fractionated using Ficoll-Paque (Pharmacia) to collect mononuclear cells. The mononuclear cell fraction was further selected for viable and invasive carcinoma cells by differential adhesion to the cell-adhesion matrix. Briefly, mononuclear cells were suspended in the complete culture medium (to same volume as the blood). A portion of mononuclear cells were seeded, i.e., 0.1-ml per well of 96-well microtiter plate or 1 to 10 ml per well of 6-well tissue culture plate (NUNC) that were coated with the collagen matrix, for 15 minutes to 1 hour. The culture was washed gently with medium to remove non-adherent cells. For immunocytochemistry and functional assays, cells in microtiter plates were cultured for 12-24 hours before processing. For cell separation studies, cells adherent on the matrix were then suspended with trypsin/EDTA solution (GIBCO) for 5 minutes or simply by vigorously washing with phosphate buffered saline (PBS). Cells in the washes were transferred into a 6-well tissue culture plate and cultured for 12 hours to 24 days in a $CO_2$ incubator at 37° C. It should be noted that, in case of patients with high white blood cell count, i.e., patients with lymphoma or leukemia, the mononuclear cell fraction should be diluted with the complete medium to 1-2 million cells per ml for one well of 6-well tissue culture plate. Recovery of cancer cells is dependent on cell density on the matrix (see below). Viability of the cells was evaluated by Trypan Blue exclusion or apoptosis assays.

Alternatively, whole blood is deprived directly of viable and invasive carcinoma cells by passing through cell culture beads coated with a cell-adhesion matrix such as type I collagen or filters made of purified cotton. A sterile 30-ml pipette was packed with purified cotton or collagen-coated beads, and 0.1-ml of collagen-coated bead was used for every 10-ml blood that was pre-diluted with equal volume of medium containing 0.5 mM EDTA or with 10% anticoagulant citrate dextrose (ACD, Bakter Healthcare Corporation, IL) containing 50 units heparin/mL. The column was pre-washed by medium containing 10% human plasma or serum. Flow rate, from 0.1 to 0.7 ml per minute, results in capture of cells that share similar features as these derived from the substratum method described above.

6.1.4 Labeling of Collagen Matrix and Measurement of the Cell Invasive Phenotype Collagen was polymerized prior to biotin, fluorescein or rhodamine labeling so that sites of polymerization were not perturbed. Labeled collagen fibers were then solubilized in acidified water (pH 2.0), but could be readily polymerized back to collagen fibers under experimental conditions. Specifically, 10 ml type I collagen solution (rat-tail type I collagen, 4 mg/ml, Collaborative Biomedical Products, Becton and Dickinson Labware, Bedford, Mass.) was mixed with 10-ml DMEM and added into a 10 centimeter tissue culture plate at 4° C. The plate was incubated for 30 min at 37° C. to allow polymerization of the collagen fibers (gel). The gel was washed with 30 ml of coupling borate buffer, pH 9.3 (Sigma) for 30 min and then incubated with 30 ml borate buffer containing 3 mg of Sulfo-NSH-Biotin (Pierce), Fluorescein Isothiocyanate I hydrochloride (FITC), Tetramethyl Rhodamine Isothiocyanate (TRITC) (Research Organics Inc, Cleveland, Ohio) or 1 mg of Bodipy-rhodamine or fluorescein dyes (Molecular Probes, Inc.), at 25° C. on a shaker. Conjugation was stopped by washing 3 times with PBS, followed by a 50-ml PBS washing for 2 days and a 50-ml distilled water wash for another 2 days. Labeled collagen fibers were solubilized in acidic water (0.02N acetic acid) to a final concentration of 1 mg/ml. Labeled collagen monomers were mixed with equal volume of unlabeled collagen solution, and further diluted with 2× volume of DMEM, overlaid on vessel surfaces to form a thin layer, and incubated for 30 min at 37° C. to allow gel formation.

Labeled collagenous matrix was coated on a 16-well microtiter plate-glass slide (in 96-well microtiter plate format; Lab-Tek, Rochester, N.Y.) or 6-well tissue culture plate (NUNC). A portion of mononuclear cells, i.e., 0.1-ml per well of 96-well microtiter plate or 1.6-ml per well of 6-well tissue culture plate (NUNC), were seeded on such substratum and cultured for 15 minutes to 1 hour to capture adherent cells. After washing of non-adherent cells, the cells were grown on the labeled matrix for 12 to 24 hours for measurement of cellular invasiveness using Nikon Eclipse E300 inverted light microscope in conjunction with SONY DC5000 Cat Eye Imaging system or Molecular Devices fMax Fluorescence Microplate Reader in conjunction with SOFTmaxPRO 1.2F for Windows software computer analysis as depicted in FIGS. 1A, 1B. Initially, the Bodipy-fluorescent collagen substrata described above were prepared in 16-well culture chambers to optimize cell culture and microscopic imaging analysis conditions for characterization of the invasiveness of the matrix-isolated cells (FIG. 1A). Substrate preparations were then optimized for 96-well microtiter plate version. Optimization parameters include feasibility for sample throughputs, and resolution for accuracy of quantitation.

6.1.5 Other Cellular Function Assays

A functional assay was performed for endothelial cell activity using acetylated low-density lipoprotein (acLDL) Bodipy FL conjugate as described in manufacture manual (L-3485, Molecular Probes, OR, USA). To resolve blood cells co-isolated on the matrix that were apoptotic or necrotic, the cells were stained prior to fixation using Vybrant Apoptosis Assay Kit #5 Hoechst/prodidium iodide (V-13244, Molecular Probes, OR, USA).

6.1.6 Cell Lines and Culture

The human breast carcinoma cell lines MDA-MB-436 and Hs578T were obtained from American Type Culture Collection (Rockville, Md.), and the human amelanotic melanoma cell line LOX was obtained from Professor Oystein Fodstad, Institute for Cancer Research, The Norwegian Radium Hospital, Oslo, Norway. Cells were cultured in a 1:1 mixture of Dulbecco's modified Eagle's medium (DMEM) and RPMI1640 supplemented with 10% calf serum, 5% Nu-serum (Collaborative Research, Inc., Bedford, Mass.), 2 mM L-glutamine, 0.1 mM non-essential amino acids, 1 mM sodium pyruvate, 1 unit/ml penicillin, and 10 µg/ml streptomycin. These cells were used to evaluate the reagents for immunocytochemical detection and to determine sensitivity of functional assays.

6.1.7 Sample Preparation for Immunocytochemistry

In order to enumerate transformed epithelial cells in the blood as compared to leukocytes and peripheral blood tissue cells, the mononuclear cells derived from blood of cancer patients that were captured by labeled collagenous matrix coated on a 16-well chambered glass slides (Lab-Tek, Rochester, N.Y.) and cultured on the same substratum for 12-24 hours in a $CO_2$ incubator at 37° C. were fixed for immunocytochemistry. Primary mAbs used in this study include mouse mAb recognizing human epithelial specific antigen (ESA; clone VU-1D9, NeoMarkers, CA, USA; SIGMA, MS, USA), Muc-1 epithelial membrane glycoprotein (Muc-1; clone E29, NeoMarkers, CA, USA), cytokeratins 4, 5, 6, 8, 10, 13, and 18 (PCK; clone C-11, SIGMA, MS, USA); CD31/PECAM-1 endothelial cell marker (CD31; Clone JC/70A, NeoMarkers, CA, USA), Flk-1, a receptor for vascular endothelial growth factor (Flk-1, Clone sc-6251, Santa Cruz, USA), VE-cadherin endothelial marker (VE-cad; Clone sc 9989, Santa Cruz, USA); CD34 peripheral blood stem cell marker (CD34; clone 581, Pharmingen, USA), CD45 leukocyte common antigen (CD45; clone T29/33, DAKO, Denmark), CD8 suppressor T cell marker (CD8; clone c8/144B, NeoMarkers, CA, USA), CD43 T cell marker (CD43; clone 84-3C1, NeoMarkers, CA, USA), prostate specific acid phosphatase (PSAP; clone PASE/4LJ, NeoMarkers, CA, USA), prostate specific antigen (PSA; clone ER-PR8, NeoMarkers, CA, USA), c-erbB-2/Her-2/neu oncoprotein (erB-2; clone e2-4001+3B5, NeoMarkers, CA, USA), c-erbB-2 (Clone TAB250, Zymed, CA, USA), CA 19-9/sialyl Lewis GI tumor marker (CA19-9; clone 121 SLE, NeoMarkers, CA, USA), or p53 tumor suppressor protein (p53; clone DO-7+BP53-12, NeoMarkers, CA, USA). In addition, fluorescein conjugated antibodies against Muc-1 epithelial cell marker (DAKO, Denmark) and fluorescein conjugates of goat antibodies against factor VIII endothelial marker (F8; Atlantic) were used to doubly stain carcinoma and endothelial cells, respectively, in addition to above primary antibodies against other cell markers. Furthermore, rat mAbs D28 (against seprase), E19, E26 (against DPPIV) and C27 (against β1 integrin) generated in our laboratory were used.

Antibody staining involves the addition of primary antibody and/or fluorescein-F8 or -Muc-1 to the slides after blocking nonspecific binding sites with 2% BSA for 30 min. The samples were incubated for 20 min at room temperature, washed twice in PBS for 5 min, and then exposed to secondary rabbit anti-mouse Ig (Z0259, Dako) for another 20 min. After two more washes, the samples were incubated with alkaline-phosphatase-anti-alkaline-phosphatase (APAAP) mouse Ig complexes for 15 min. Finally, the enzyme-substrate [NewFuchsin (Dako)] was added, resulting in the development of red precipitates. The data were recorded by using Nikon Eclipse E300 inverted light microscope in conjunction with SONY DC5000 Cat Eye Imaging system and were stored on a computer server for later reference.

6.1.8 Sample Preparation for Flow Cytometric Analysis

In order to enumerate transformed epithelial cells in the blood that were captured by labeled collagenous matrix coated on a 6-well tissue plate, the mononuclear cells released from the matrix substratum were analyzed by flow cytometry following a manufacture's procedure. Similar to procedures involved in immunocytochemistry, the cells were determined for apoptosis or necrosis by staining prior to fixation using Vybrant Apoptosis Assay Kit #5 Hoechst/prodidium iodide (V-13244, Molecular Probes, OR, USA). Briefly, the mononuclear cells were stained in a solution containing fluorescein (FITC)-conjugated mouse mAb C11 against cytokeratins 4, 5, 6, 8, 10, 13, 18 (PCK; Sigma) or fluorescein-antibodies against Muc-1 (DAKO), phycoerythrin (PE)-conjugated anti-CD31 endothelial marker (CD31; Becton-Dickinson) and peridinin chlorophyll protein (PerCP)-labeled anti-CD45 (CD31; Becton-Dickinson) for 15 min. After incubation and washing, the collected cells were resuspended in 0.5 ml of a buffer and the sample was analyzed on a FACScan or FACS-Vantage flow cytometer (Becton Dickinson).

6.2 Results

6.2.1 Isolation of Cancer Cells Using the Cell-Adhesion Matrix: Role of Blood Borne Cell Adhesion Molecules Table I shows the attachment of LOX human malignant melanoma cells and cancer cells isolated from a patient with head-neck cancer to various natural fiber surfaces in the presence of human plasma fibronectin, laminin and vitronectin, as well as human and bovine sera. Attachment of human cancer cells were assayed in 96-well plates (Nunc, Inc., Naperville, Ill.) coated with either various amounts of purified serum proteins (0.1 to 1 μg per well) or 10% serum and was performed as described (Nomizu et al., 1995). Cell attachment properties of natural fibers were determined by counting the number of cells in the area that remained attached on 1.27 mm² areas of a microtiter well. In the presence of human or bovine sera or fibronectin+laminin+vitronectin, LOX melanoma cells adhere better on purified collagen, fibrin, and cotton fibers, as well as lined plastic surfaces than plain plastic, and have higher numbers of cells that remain attached (Table 1). Similarly, head-neck cancer cells attach better on purified collagen, fibrin, and cotton fibers, as well as lined plastic surfaces than plain plastic, and have higher numbers of cells that remain attached (Table 2). These results suggest that the surfaces of the cell-adhesion matrix exert their effects on cancer cell adhesion through their binding affinity for blood-borne adhesion molecules.

TABLE 1

Attachment of LOX melanoma cells on various cell-adhesion matrix surfaces is mediated primarily by binding of the matrix to blood-borne cell adhesion molecules.

| | Human serum | Bovine serum | FN + LM + VN | Negative control |
|---|---|---|---|---|
| Type I collagen | 92 ± 5 | 91 ± 6 | 86 ± 5 | 8 ± 5 |
| Fibrin | 68 ± 7 | 72 ± 8 | 67 ± 6 | 6 ± 6 |
| Purified cotton | 79 ± 5 | 83 ± 9 | 72 ± 6 | 7 ± 6 |
| Lined plastic | 57 ± 8 | 49 ± 9 | 35 ± 8 | 4 ± 3 |
| Plain plastic | 7 ± 3 | 5 ± 4 | 3 ± 2 | 2 ± 1 |

Cells, 4×10³ per well (the number of cells in the area that remained attached on 1.27 mm² areas of a microtiter well was counted), were seeded on various matrix surfaces in 96-well plates (Nunc, Inc., Naperville, Ill.), that were coated with 10% human serum (Sigma), 10% bovine serum (Collaborative Research, Inc., Bedford, Mass.), or human plasma fibronectin+laminin+vitronectin (FN+LM+VN; Gibco-BRL, Gaithersburg, Md.) at the concentration of 10 μg/ml each. The wells that were not coated with protein were used as negative control. Type I collagen fibers were formed on the bottom of microtiter wells according to the procedure described below. Fibrin fibers were made by clotting 20% human plasma in Dulbecco's modified Eagle's medium in microtiter wells. Purified cotton fibers were also suspended in Dulbecco's modified Eagle's medium and seeded in microtiter wells. "Lined plastic" indicates that the surface of microtiter wells had been scrapped with an Eppendorf peptide tip. Each value represents the mean±S.D. of three independent experiments.

TABLE 2

Attachment of head-neck cancer cells on various cell-adhesion matrix surfaces is mediated primarily by binding of the matrix to blood-borne cell adhesion molecules.

| | Human serum | Bovine serum | FN + LM + VN | Negative control |
|---|---|---|---|---|
| Type I collagen | 42 ± 4 | 41 ± 4 | 37 ± 5 | 2 ± 2 |
| Fibrin | 37 ± 3 | 33 ± 5 | 27 ± 3 | 3 ± 2 |
| Purified cotton | 38 ± 5 | 34 ± 4 | 29 ± 2 | 2 ± 1 |
| Lined plastic | 27 ± 2 | 28 ± 3 | 22 ± 2 | 2 ± 1 |
| Plain plastic | 5 ± 2 | 3 ± 2 | 2 ± 1 | 2 ± 1 |

Cells, 2×10³ per well (the number of cells in the area that remained attached on 1.27 mm² areas of a microtiter well was counted), were seeded on various matrix surfaces in 96-well plates (Nunc, Inc., Naperville, Ill.), that were coated with 10% human serum (Sigma), 10% bovine serum (Collaborative Research, Inc., Bedford, Mass.), or human plasma fibronectin+laminin+vitronectin (FN+LM+VN; Gibco-BRL, Gaithersburg, Md.) at the concentration of 10 μg/ml each. The wells that were not coated with protein were used as negative control. Type I collagen fibers were formed on the bottom of microtiter wells according to the procedure described below. Fibrin fibers were made by clotting 20% human plasma in Dulbecco's modified Eagle's medium in microtiter wells. Purified cotton fibers were also suspended in Dulbecco's modified Eagle's medium and seeded in microtiter wells. "Lined plastic" indicates that the surface of microtiter wells had been scrapped with an Eppendorf peptide tip. Each value represents the mean±S.D. of three independent experiments.

6.2.2 Sensitivity of Cell Separation Methods

The human invasive breast carcinoma cell lines MDA-MB-436 and Hs578T (American Type Culture Collection, Rockville, Md.) were used to determine sensitivity of the cell separation method and to evaluate the reagents for immuno-cytochemical detection (see below). These breast cancer cells were tagged with a fluorescent dye to determine the sensitivity of the isolation procedure. FIG. 3A-G show the analysis of normal and bladder cancer blood samples to which varying numbers of Hs578T breast carcinoma cells, which were tagged with PKH26 Red Fluorescent Cell Linker (Sigma), were added. As can be seen, the carcinoma cells can be distinguished from the other blood cells. The recovery of breast carcinoma cells was consistent over a frequency range, between 1 and 500 Hs578T cells spiked into 1-ml of blood (10-20 million mononuclear cells per ml) from normal donors, and the recovery rate was between 75 and 100%. However, when Hs578T breast carcinoma cells were spiked into the blood from a bladder cancer donor with less than 10 million mononuclear cells per ml, the recovery of the Hs578T cells was between 95 and 100%, suggesting cell density is a limiting factor for cell adhesion to the matrix. In addition, when 19 red fluorescent tagged Hs578T cells were spiked into 1-ml of blood from a bladder cancer donor, both isolated Hs578T and bladder cancer cells were identified by positive staining with anti-cytokeratin antibody C11 (FIG. 3E-3F). There were 16 fluorescent tagged Hs578T cells and 468 bladder carcinoma cells detected in one ml blood. These results suggest that the level of sensitivity by the matrix capture method is at 1 viable cancer cell per ml of blood, and the recovery rate can reach 85%.

6.2.3 Cancer Cell Isolation Using the Cell-Adhesion Matrix

For detection of cancer cells in blood, a thin layer of rhodamine-collagen solution coated on 16-well chambered glass slides (Lab-Tek, Rochester, N.Y.) or 96-well culture plates (NUNC), which is subsequently incubated with calf serum containing blood-borne adhesion molecules, is a preferred embodiment of the "matrix". Mononuclear cells in buffy coat derived from 1.6 millimeter (ml) of whole blood are seeded in equal aliquots, 0.1 ml each, into each well of a 16-well chambered glass slide, and incubated for 10 minutes to 18 hours at 37° C. to select for cancer cells by differential adhesion to the collagen matrix.

FIG. 4A-D depict the isolation of circulating cancer clusters with tissue fragments using such a type I collagen based, cell-adhesion matrix. Such cell clusters of various sizes were commonly observed in the blood of patients with advanced metastatic disease, including squamous cell carcinoma of head and neck (FIG. 4A-C) and prostate cancer (FIG. 4D). It has been estimated that there are large numbers of cancer cell clusters in the blood of stage III-IV cancer patients, ranging from a few hundred to twenty thousand per cubic centimeter of blood. However, there are no such cell clusters found in the blood of normal donors or early stage cancer patients. Furthermore, fibrin fibers (FIG. 4E), plastic scraps (FIG. 4F-G), purified cotton fibers (FIG. 4H-I), and type I collagen fibers (FIG. 5A-H) capture circulating carcinoma cells that grow in culture and exhibit epithelial cell shape. Surfaces of these materials absorb blood-borne cell adhesion molecules, which in turn promote the attachment and spreading of tumor cells (see Table II above). The role of cell adhesion molecules in this process has been further demonstrated by incubation of coated collagen matrix with polyclonal antibodies directed against fibronectin, vitronectin, and laminin. This treatment resulted in a reduction of cell capture capability of the matrix.

FIG. 5A-H show the morphology of circulating cells and their underlying type I collagen-based, cell-adhesion matrix in the presence of blood-borne cell adhesion molecules. These carcinoma cells adhere preferentially to the collagen matrix within 10 minutes to 60 minutes after contact. They then degrade and ingest the matrix generating holes on flat substrata, followed by migration and growth on the plastic surface (FIGS. 5A-D; 6A-D). Such carcinoma cells are not present in blood of most normal donors (FIG. 7A), patients with benign disease (FIG. 7B), or cancer patients undergoing chemotherapy (FIG. 7C-D). Freshly isolated circulating cancer cells are small in size but relatively larger than most of mononuclear blood cells co-isolated on the matrix (FIG. 6A). These putative cancer cells grow rapidly, become larger in size, and assume epithelial shape within four days in culture (FIGS. 5A-D; 6A-D). However, co-isolated leukocytes are small and reduce their number in culture (FIG. 5A-D). Also, few carcinoma cells isolated from squamous cell carcinoma of head and neck biopsies (SCCHN) using the cell-adhesion matrix (FIG. 5E-F) exhibited the invasive phenotype or growth characteristics of circulating cancer cells, suggesting that circulating cancer cells represent a unique subset of carcinoma cell population that metastasizes. In such SCCHN tissue, they are fibroblasts that invade the collagen gel and propagate in culture (FIG. 5E-F). It should be noted that the cell separation system captures cells which remain viable, i.e., cells which retain the ability to adhere, but not those that are damaged in the circulation or by experimental manipulation.

The thickness of the collagen matrix was estimated approximately 100 μm, as determined by both light microscopic and transmission electron microscopic measurements (FIG. 5E-H). The assembled collagen can capture cancer cells from mixed cell population, i.e., blood or cell suspension derived from tissue biopsy, within 10 minutes to one hour. The matrix-captured cells can further invade into the matrix during the one to two week incubation, leaving behind some non-invasive cells, which do not multiple, on the surface of the matrix (FIG. 5E-F). The assembled collagen fibers are fine strings of 70 nm in diameter and have similar appearance as these in the collagen bundles in vivo except they lack the collagen-banding pattern (FIG. 5G-H).

6.2.4 Functional and Immunophenotypic Features of Circulating Cancer Cells

The functional and immunophenotypic features of the epithelial cells captured by the matrix are consistent with those of neoplastic cells. For measurement of the invasive phenotype of these cells, cells that were isolated from blood of cancer patients using rhodamine-collagen matrix were analyzed for the ability of the cell to adhere to, degrade and ingest rhodamine-collagen substratum. FIG. 8A-I show that putative carcinoma cells exhibit extensive collagen-degrading/ ingestion activities (Col+); these cells also exhibit immuno- and morphological features characteristic of carcinoma cells (see below).

For the determination of nature of cancer cells, cells that were isolated from blood of cancer patients using rhodamine-collagen matrix were analyzed for their potential epithelial origin by immunocytochemistry using antibodies against epithelial specific antigen (ESA), epithelial membrane antigen (Muc-1), and cytokeratins 4, 5, 6, 8, 10, 13, and 18 (PCK). These cells react positively with ESA+, Muc-1+, or PCK+ are epithelial origin, and therefore, consistent with their metastatic nature. On the matrix, adherent cells including enriched cancer cells are stained with cell type-specific monoclonal antibodies such as these against epithelial, carcinoma, endothelial, peripheral blood stem cells, or leukocytes. Adherent cells, that are labeled positively for epithelial cell markers (FIGS. 8E, G, J, K) and that ingested collagen fragments, Col+ (FIGS. 8B, C, F, I, L), are identified as carcinoma cells. Circulating carcinoma cells are rare in blood of most normal donors (FIG. 8L), patients with benign disease, or cancer patients undergoing chemotherapy. Similar to immunocytochemical analysis presented here, mononuclear cells derived from blood of cancer patients that were released from the matrix can be subject to fluorescence-activated cell sorting (FACS) analysis.

6.2.5 The Acquisition of an Endothelial Cell Phenotype by Circulating Carcinoma Cells In addition to invasion, metastatic carcinoma cells in the circulation involve an apparently novel angiogenic propensity. Circulating carcinoma cells isolated from the blood of cancer patients using a cell-adhesion matrix inevitably acquire endothelial characteristics. These squamous cell carcinoma of head-neck (HN, FIGS. 9A-C; 9I-J), colon cancer (CC, FIG. 9D-E) and prostate cancer (PC, FIG. 9G-H) cells are Col+ (FIGS. 9C, F), stain for the endothelial cell markers, including von Willebrand factor or factor VIII (F8) (FIGS. 9B, E) and CD31 (FIG. 9D), and express an endothelial cell ability by incorporating acetylated low-density lipoprotein (LDL) (FIGS. 9H, J) as well as an epithelial surface antigen (ESA in FIG. 9G). In addition, when the isolated carcinoma cells internalized and were labeled with fluorescein-LDL and then plated on a collagen gel of 0.5-mm in thickness, they showed enhanced endothelial differentiation, including the formation of cellular networks and tube-like structures (FIGS. 9K, L). These structures consisted principally of LDL-labeled carcinoma cells. Furthermore, circulating carcinoma cells illustrate additional endothelial features including the expression of the receptor for vascular endothelial growth factor Flk-1 and VE-cadherin, and without loss of previously expressed epithelial markers. This angiogenic propensity is restricted to those carcinoma cells that enter the circulation and not with cells that remain in the tumor tissue. Such spatial restriction in angiogenic phenotype reflects distinct functional abilities of circulating carcinoma cells to extravasate, colonize and cooperate with angiogenesis that lead to formation of micrometastases.

6.2.6 Immune Cancer Killing and Growth of Circulating Cancer Cells in Culture Circulating cancer cells form clusters with white blood cells (WBC) that express the leukocyte common antigens CD45 and the T-cell marker CD8. The cell-adhesion matrix could readily isolate such clusters of immune and cancer cell complex from cancer patients who exhibited encouraging prognosis. Although total number of circulating cancer cells may indicates a potential for metastasises formation, numerations of the cancer cells that interact with cytotoxic WBC (FIG. 10A-I) or autoimmune anti-cancer antibody-mediated, complement cytolysis (FIG. 10J-L) signify the host immunity against metastasis. In these cancer patients who exhibited favorable prognosis, most cancer cells were attacked by leukocytes and became fragmented after one day in culture and only a few cancer colonies grew (FIG. 10F-I). In addition, anti-cancer antibody-mediated complement cytolysis can take place in most cancer patients. Such killing of cancer cells was demonstrated here by culturing isolated BLC cells in the presence of 10% autologous plasma, derived from the blood of the same cancer patient (FIG. 10J-K), but not in those from a normal donor (FIG. 10L). Resulting cytolysis of cancer cells can be determined by morphological appearance of phase-dark materials in lysed cells (FIG. 10J-L). Importantly, approximately 97% cells freshly isolated from the blood are apoptotic as determined by fluorescent staining using apoptosis and cell lyses kits produced by Molecular Probes, Inc. Although some cancer cells can propagate in the culture for two months, most cancer cells show apoptosis or cytolysis immediately after their isolation, indicating cancer cell killing by host immunity. Most WBC disappear from the culture after one week, leaving behind clusters or colonies of cancer cells (FIG. 10E-L). Thus, numeration of viable and invasive cancer cells that resist immune killing would be the strongest indicator for patients who process high degree of malignancy.

6.2.7 Enumeration of Circulating Cancer Cells

Circulating cancer cells isolated using the cell separation methods were analyzed for their invasive activities, epithelial nature, angiogenic propensity, and resistance to host immunity as described above. Results were recorded using an inverted Nikon microscope computerized with a SONY DKC5000 3CCD imaging system. Numeration of cancer cells present in whole blood or buffy coat by this cell separation and assay methods described herein presents the highest sensitivity and resolution. Over 200 blood samples of patients with prostate, breast, colon, lung, head & neck, brain, bladder, lymphoma, renal & testis, liver, or pancreatic and other gastrointestinal cancers were examined. Circulating cancer cells, as defined by Col+, LDL+, ESA+, Muc-1+, PCK+, F8+, or CD31+ cells, are in the order of two thousand to twenty thousand per ml of whole blood derived from cancer patients with metastatic diseases. From this study, it is estimated that there are 8 to 80 million viable cancer cells in the circulation of a cancer patient which have the potential to metastasize. This is over 100-fold higher resolution than previous antibody-based approach (Racila, E., Euhus, D., Weiss, A. J., Rao, C., McConnell, J., Terstappen, L. W., and Uhr, J. W., 1998, Detection and Characterization of Carcinoma Cells in the Blood. Proceedings of the National Academy of Sciences of the United States of America 95, 4589-4594). However, the number of metastatic cells estimated from this study represents only 0.1% of total circulating cancer cells as reported in a previous investigation (Glaves et al., 1988, Br. J. Cancer 57:32-35).

7. EXAMPLE

Regulation of Fibroblast Migration on a Collagenous Matrix is Dependenton a Novel Cell Surface Protease Complex The data provided below, demonstrates that the formation of a novel protease complex, consisting of serine integral membrane proteases (SIMP), including seprase and dipeptidgl peptidase IV (DPPIV), at invadopodia of migrating fibroblasts is associated with cell invasion and migration on a collagenous matrix.

7.1 Materials and Methods

7.1.1 Cell Culture

The human embryonic lung fibroblastic line WI38 and human breast carcinoma cell line MDA-MB-436 were obtained from American Type Culture Collection (Rockville, Md.). Cells were cultured in a 1:1 mixture of Dulbecco's modified Eagle's medium (DMEM) and RPMI1640 supplemented with 10% calf serum, 5% Nu-serum (Collaborative Research, Inc., Bedford, Mass.), 2 mM L-glutamine, 1 unit/ml penicillin, 10 g/ml streptomycin, 0.1 mM non-essential amino acids and 1 mM sodium pyruvate. Rat mAbs E26, E19 and F4 are directed against human placental DPPIV, rat mAbs D8 and D28 are against human placental seprase (Goldstein L A et al., 1997, *Biochim. Biophys. Acta.* 1361:11-19; Pinereiro-Sanchez, M L et al., 1997, *J. Biol. Chem.* 272: 7595-7601; correction (1998) *J. Biol. Chem.* 272:13366), mAb C27 is directed against human melanoma β1 integrin and rat mAb C37 is directed against cell surface glycoprotein gp-90 (Meuller, S C., et al., 1999, *J. Biol. Chem.* 274:24947-24952). Mouse anti-αv integrin and anti-β3 integrin mAbs were from American Type Culture Collection (clone L230, catalog number HB8448 and clone AP-3, catalog number HB242, respectively).

7.1.2 Isolation of Seprase-DPPIV Complex

WI38 cells were seeded onto hydrated type I collagen films (rat tail type I collagen at 0.2 mg/ml, Collaborative Biomedical Products, Becton and Dickinson Labware, Bedford, Mass.) and cultured until 90% confluence. Surface biotinylation of WI38 monolayers were performed using Suffo-NSH- Biotin (Pierce, Rockford, Ill.) according to manufacturer's instructions. To harvest lysates, each culture plate was washed 3 times with PBS and extracted with 125 l/cm$^1$ of RIPA solution (1.25% Nonidet P-40, 0.5% sodium deoxycholate, 0.1% SDS in 50 mM Tris buffer, pH 7.5). Extraction was performed for 2 h at 25° C., 25 rpm on a rotary shaker (Bellco Orbital Shaker, Vineland, N.J.). The cell layer and buffer were removed and transferred to a 50 ml conical tube and incubated a further 3 h at 4° C. with end-over-end agitation. The extract was clarified by centrifugation at 10,000×g for 20 min at 4° C. and the supernatants used for immunoprecipitation reactions.

To prepare immunoaffinity matrix, purified rat mAbs against membrane proteins (2.5 mg) were coupled to 1-ml CNBr-Sepharose 4 MB (Pharmacal Biotech Inc., Piscataway, N.J.). 0.25-ml mAb-beads were used to immunoprecipitate complexes from 25-ml cell extract overnight at 4° C. with end-over-end agitation. After 3 washes in 25 ml of extraction buffer, the beads with coupled antibody-antigen complexes were resuspended in 0.1% glycine-HCl (pH 2.4) buffer (equal to the bead volume) and the sample was incubated for 5 min at 4° C. Immediately, the sample was transferred to an Amicon filter insert (0.45 m 400 l capacity) and centrifuged 10 min at 10,000 rpm in an Eppendorf microfuge at 4° C. The bead filtrate was neutralized by addition of 2M Trizma base. To determine the subunit composition of isolated protein complexes, immunoprecipitates of the surface-biotinylated complexes were analyzed for their protein profiles by SDS-PAGE, transferred to nitrocellulose membranes and detected with HPR-streptavidin (Sigma, St. Louis, Mo.) and the ECL system (Amersham, St. Louis, Mo.). Isolated protein complexes were also used for immunoblotting (with anti-seprase, -DPPIV, -β1 and -β3 integrin mAbs), for gelatin zymography (to detect seprase gelatinase activity), and for DPPIV substrate membrane overlay as described (Pinereiro-Sanchez, M L et al., 1997, *J. Biol. Chem.* 272: 7595-7601; correction (1998) *J. Biol. Chem.* 272:13366). To test for complete elution of proteins from the beads, Laemmli sample buffer (equal to the bead volume) was added and samples were heated by microwaves (2 cycles on low setting 30 sec each, followed by 1 cycle on medium for 30 sec). Then, the samples were immediately centrifuged at 4° C. The filtrates were subjected to assays described above.

7.1.3 Labeling of Collagen Fibers

Collagen was polymerized prior to biotin, fluorescein or rhodamine labeling so that sites of polymerization were not perturbed. Labeled collagen fibers were then solubilized in acidified water (pH 2.0), but could be readily polymerized back to collagen fibers under experimental conditions. Specifically, 10 ml type I collagen solution (rat-tail type I collagen, 4.66 mg/ml, Collaborative Biomedical Products, Becton and Dickinson Labware, Bedford, Mass.) was mixed with 10-ml DMEM at 4° C. The mixture was incubated for 30 min at 37° C. to allow polymerization of the collagen fibers (gel). The gel was washed with 30-ml of coupling borate buffer, pH 9.3 (Sigma) for 30 min and then incubated with 30-ml borate buffer containing 3 mg of Sulfo-NSH-Biotin (Pierce), Fluorescein Isothiocyanate I hydrochloride (FITC) or Tetramethyl Rhodamine Isothiocyanate (TRITC) (Research Organics Inc, Cleveland, Ohio) at 25° C. on a shaker. Conjugation was stopped by washing 3 times with PBS, followed by a 50-ml PBS washing for 2 days and a 50-ml distilled water wash for another 2 days. Labeled collagen fibers were solubilized in acidic water (0.02N acetic acid) to a final concentration of 1 mg/ml. Labeled collagen monomers were mixed with equal volume of DMEM or p-buffer (300 mM NaCl in 50 mM ammonium bicarbonate buffer, pH 8.4) and incubated for 30 min at 37° C. to allow gel formation.

7.1.4 Cell Migration and Fluorescent Collagen Degradation Assays

Fluorescent collagen fibers overlaying a monolayer wound culture were used to examine cell migration in collagen gel during wound closure. WI38 cells were grown in 2-well chambered cover slips (Lab-Tek, Rochester, N.Y.) to confluence. The monolayer was scratched with a pipette tip to generate wound edges. Culture media were then replaced with TRITC-collagen in DMEM (600 g/ml; 50 l/well) and the culture allowed to gel in a $CO_2$ incubator for 30 min at 37° C. Media containing serum or inhibitory mAbs (300 l/well) were then added and their effects on cell migration and collagen degradation in real time were observed using phase contrast and fluorescence microscopy (Nikon Inverted Microscope). Cell migration and collagen degradation were quantified by measuring the areas of cell migration and fluorescent collagen removal by migratory cells using NIH Image 1.62b4/fat analysis program.

A microtiter version of the above assay was developed to measure collagen degradation by migratory cells. In a 96-well tissue culture plate (Nunc, Rochester, N.Y.), 50 l/well of TRITC-collagen solution (600 g/ml) was first loaded and the solution allowed to gel in 37° C. incubator for 30 min. The TRITC-collagen gel was then overlaid with 50 l/well of the TRITC-collagen solution containing $2 \times 10^5$ cells and mAbs (50 g/ml), and the culture allowed to gel in a $CO_2$ incubator for 30 min at 37° C. The culture was then supplemented with 150 l fresh media per well. All media were prepared free of phenol red. At times 100 l of culture media from each well was removed to measure the release of TRITC-collagen peptides using a fluorescent microplate reader with excitation at 544 nm and emission at 590 nm (Molecular Devices fMax: Fluorescence Microplate Reader). Leucine incorporation was used to determine metabolic activities of cells in culture conditions, in which 150 l/well of media containing 2 Ci/ml $^3$H-Leucine was added into the culture, and the cell-collagen layers were solubilized in 5 ml of scintillation fluid and counted in a scintillation counter (Beckman LS-7500).

Stable transfectants of the breast carcinoma line MDA-MB-436 that expresses constitutively seprase and DPPIV were obtained. Plasmid pA11 (pCR3.1 vector alone), pA15 (vector plus full length seprase), and pZ8 (DPPIV ribozyme construct) were transfected into MDA-MB-436 cells using lipofectamine (Gibco/BRL) following the manufacture's instructions. The selection medium contained G418 at a concentration of 300 g/ml.

7.1.5 Immunofluorescent Labeling of Seprase and DPPIV

WI38 cells were cultured in collagen gel, fixed and immunolabeled in a single step using rhodamine conjugated mAbD28 against seprase and fluorescence conjugated mAb E26 against DPPIV as described (Meuller, S C, et al., 1999, *J. Biol. Chem.* 274:24947-24952). Stained samples were photographed using the Planapo 25/1.2 or 63/1.4 objectives on a Zeiss Photomicroscope III (Carl Zeiss, Inc.) under epifluorescence.

7.1.6 Human Gingival Wounds and Invasive Human Breast Carcinoma

Human gingival biopsies were derived from the University of Turku, Finland. Full thickness wounds of oral mucosa were made from two healthy volunteers and biopsies were collected after 3, 7, 14 and 28 days of wounding. Immediately after biopsy, fresh tissue blocks were mounted in Histoprep® (Fisher Scientific, New Jersey) and snap frozen in liquid nitrogen. Frozen sections (6 m) were cut, fixed with −20° C. acetone for 5 min, and stored at −70° C. For routine histology, the sections were stained with hematoxylin and eosin. For immunohistochemical staining, sections were washed with PBS containing 0.1% bovine serum albumin (BSA; Sigma Chemical Co., St. Louis, Mo.) and incubated with rhodamine-conjugated mAb D28 against seprase in PBS/BSA in humid chamber at 4° C. for 16 h. The sections were then washed with PBS/BSA and water, briefly air-dried, and mounted using cyanoacrylate glue (Krazy Glue, Borden Company LTD). The staining was examined using a Zeiss Axioskop 20 light, fluorescence and confocal microscopy, and photographed using MC 80 Zeiss microscope camera. Control staining was performed with rhodamine-conjugated secondary antibody and showed no specific stain. Immunohistochemical staining of invasive human breast carcinoma was performed as described (Kelly T et al., 1998, *Mod. Pathol.* 11:855-863).

7.2 Results

The data presented indicates that like seprase in LOX human malignant melanoma cells (Pineiro-Snachez M L, 1997, *J. Biol. Chem.* 272:7595-7601), the majority of seprase and DPPIV in WI38 human embryonic fibroblasts were present as a >400-kDa complex in non-ionic detergents, including Triton X-100, Triton X-114, RIPA buffer containing 0.1% sodium dodecyl sulfate (SDS), and octyl glucoside, and in WGA-agarose affinity-purified material. The >400-kDa complex eluted in the void volume fractions on Sephacryl S-200 gel filtration chromatography. Isolation of WGA-purified material followed by Superose 12 gel filtration liquid chromatography, exhibited major forms of about 200-kDa (Fraction 17), 440-kDA (Fraction 14), and 670-kDa (Fraction 13) (FIG. 11A). As seprase contains a 97-kDa subunit and DPPIV a 110-kDa monomer and as both seprase and DPPIV are dimers in non-ionic detergents (10), the gel filtration data suggests the presence of the seprase-DPPIV complex at 440-670 kDa sizes (FIG. 11B).

Immunoprecipitation using mAb D28 (against seprase) and mAb E19 (against DPPIV) identified two major similar intensity bands in the WI38 cell extract that was surface-biotinylated (FIG. 12A). The two bands, cross-immunoprecipitated by mAb D28 or E19, indicate seprase and DPPIV dimers, respectively. In such SDS gels when samples were solubilized in 1% SDS and not boiled, the top or slower band at 200-kDa was identified by immunoblotting as DPPIV, and the lower or faster band migrating at 170-kDa as seprase, respectively (FIG. 12B). The 350-400 kDa heteromeric aggregate was not detected in SDS gels following SDS solubilization of the sample (FIGS. 12A, 12B), suggesting that the heteromeric aggregate dissociated into two stable dimers of 200-kDa DPPIV and 170-kDa seprase, respectively. In three independent experiments involving RIPA cell extracts, a stable association of seprase and DPPIV was detected using mAbs against seprase and DPPIV but not those against β1 and β3 integrins (FIGS. 12A, 12B). Furthermore, such heteromeric complex was demonstrated by the proteolytic activities of the immuno-isolated complex. Antigens were isolated from WI38 RIPA extracts by affinity purification using either mAb D28 or mAb E19 that recognize seprase or DPPIV, respectively. The eluates were analyzed for a 170-kDa (seprase) gelatinase (FIG. 12C) and 200-kDa (DPPIV) proline-specific dipeptidyl-aminopeptidase (FIG. 12D). Gelatin zymography detected a 170-kDa gelatinase activity in immunoprecipitates of anti-seprase mAb D28 (FIG. 12C, IP: seprase) or anti-DPPIV mAb E19 (FIG. 12C, IP: DPPIV). Isolated DPPIV dimer has no gelatinase activity and the 170-kDa band on the gelatin zymogram identified with the DPPIV antibody represents the presence of seprase in the complex. Similarly, DPPIV substrate overlay assay detected a 200-kDa proline-specific dipeptidyl-aminopeptidase activity in immunoprecipitates of anti-seprase mAb D28 (FIG. 12D, IP: seprase) or anti-DPPIV mAb E19 (FIG. 12D, IP: DPPIV). No 170-kDa gelatinase of DPPIV activities could be observed for αv, α2, α6 or β3 integrin or control immunoprecipitates. These results also confirm previous observations that seprase and DPPIV are homodimers in SDS buffer, which are sensitive to heat (>60° C.) and acid for dissociation into their monomeric subunits. Thus it appears that the protease complex contained equal amounts of seprase and DPPIV proteins (FIGS. 11A, 11B, 12A, 12B), and it was equally effective in eliciting 170-kDa gelatinase and 200-kDa DPPIV dieptidyl-aminopeptidase activities (FIGS. 12C, 12D).

To determine the role of the seprase-DPPIV complex in cell migration in collagen gel and possible collagen degradation we overlaid a thin layer of collagen on a cell monolayer wound model for morphological examination and on a sparse culture for biochemical study (FIG. 13). Cell migration in collagen gel and local collagen removal by cells were measured by counting the area of cell migration/collagen removal using image analysis in conjunction with phase contrast and fluorescence microscopy (FIG. 13A-13D). Addition of mAb E19 (against DPPIV) into the wound-closure model blocked cell migration (FIGS. 13B, 13C) and local collagen removal by cells (FIG. 13D), while that of a class matched mAb (IgG) did not (FIGS. 13B, 13C, 13D). There was an increase in inhibition with increasing amounts of mAb E19 (FIG. 13B) and the antibody inhibitory effect could be reversed by removal of E19, thus, this mAb was not toxic (FIG. 13C). Furthermore, local collagen degradation by activated cells was quantified by counting fluorescent peptides released from fluorescent collagen fibers by WI38 cells in a sparse culture in a 96-well plate using spectrofluorometry (FIG. 13E). Cells in sparse culture are known to be migratory due to less "contact inhibition of migration" (Chen, W-T, 1979, *J. Cell Biol* 81:684-691). Migratory WI38 cells showed time-dependent collagen degradation within 4 days, and mAb E19 (against DPPIV) inhibited collagen degradation by migratory cells while the control mAb C37 (anti-gp-90) did not (FIG. 13E). These data demonstrate the role of the seprase-DPPIV complex in cellular migration in collagen gel and in the collagen degradation by wound-activated fibroblasts.

As DPPIV was shown to be an adhesion receptor for collagen (Bauvois B, 1988, *Biochem. J.* 252:723-731; Hanski C, 1988, *Exp. Cell Res.* 178:64-72; Loster K., 1995, *Biochem. Biophys. Res. Commun.* 217:341-348) or fibronectin (Cheng, H C 1998, *J. Biol. Chem.* 272:24207-24215; Johnson R C et al., 1993, *J. Cell Biol* 121:1423-1432; Piazza, G A et al., 1989, *Biochem. J.* 262:327-334)), it was determined whether the inhibitory effect of mAb E19 (against DPPIV) on cellular migration in collagen gel and on the collagen degradation by migratory cells is due to its influence on adhesion activity. FIG. 14 shows that, in parallel comparison to integrin adhesion to collagen fibers, while mAb E19 (against DPPIV) inhibits cellular migration in collagen gel and on the collagen degradation by migratory cells it does not affect WI38 cell spreading on collagen substratum (FIG. 14A) and attachment to collagen substratum (FIG. 14B). However, mAb C27 (against β1 integrins) inhibits WI38 cell spreading on and adhesion to collagen substratum but mAb E19 (against DPPIV) or mAb C37 (anti-gp-90) do not (FIGS. 14A and 14B). These indicate that integrins may be primary collagen receptors on WI38 cells responsible for substrate binding of the seprase-DPPIV complex.

To demonstrate that seprase and DPPIV are associated in invadapodia of migratory cells, double label, immunofluorescence experiments were performed (FIG. 15). It was observed that invadapodia of the cell migrating in collagen gel (a) were stained positively with TRITC-mAb D28 against seprase (b) or FITC-mAB E26 against DPPIV (c). Superimposed image also shows that seprase and DDPIV co-localize at the invadapodia of a WI38 fibroblast migrating in collagen gel (d).

To examine if such seprase and DPPIV co-localization could be found in vivo immunohistochemical experiments were performed on serial sections of formaldehyde-fixed, paraffin-embedded, human breast carcinoma tissue (FIGS. 16 and 18). Like tumor cells in the invasion front, connective tissue cells in human invasive breast carcinoma were strongly reactive with mAb D28 against seprase or mAB E26 against DDPIV (FIG. 16, arrows). However, such seprase and DPPIV staining was not detected in connective tissue cells of distant normal tissues (FIG. 18). It is likely that seprase-DDPIV expression associates with the activation of connective tissue cells in response to cancer invasion; and seprase and DPPIV co-localize in these activated tissue cells as well as in invasive carcinoma cells.

Unlike human umbilical cord smooth muscle cells in culture (Goldstein L A et al., 1997, *Biochim. Biophys. Acta.* 1361:11-19), both seprase and DPPIV preferentially distribute among mesenchymal cells but not differentiated muscle and endothelial cells of large vessels in human embryonic tissues, including placenta and umbilical cord. To determine if seprase and DDPIV expression in stromal fibrobalsts is induced during wound closure in vivo, the immunohistochemistry of human gingicval mucosa-wound closure was investigated (FIG. 17). A strong expression of seprase and DDPIV was seen in connective tissue cells at day 3 after wounding (b-d, g). No immuno-reaction was seen in adjacent normal mucosa tissue. No specific reaction was seen in the fibrin clot area and epithelium. Confocal microscopy shows the localization of seprase (d) and DPPIV in protrusions of connective tissue cells, which indicate the existence of invadapodia in vivo. Later, at day 7 after wounding, only a few cells in the middle of granulation tissue were reactive with the anti-seprase antibody (f) but not the anti-DPPIV antibody (h). Seprase and DDPIV staining disappeared from connective tissue cells after one week and cells of 14 or 28-day-old wounds also did not react with the antibody. The data indicates that seprase and DDPIV are activation enzymes on fibroblastic, endothelial and carcinoma cells, and that they may participate in the local collagen degradation necessary for cellular migration.

Figure 19A:
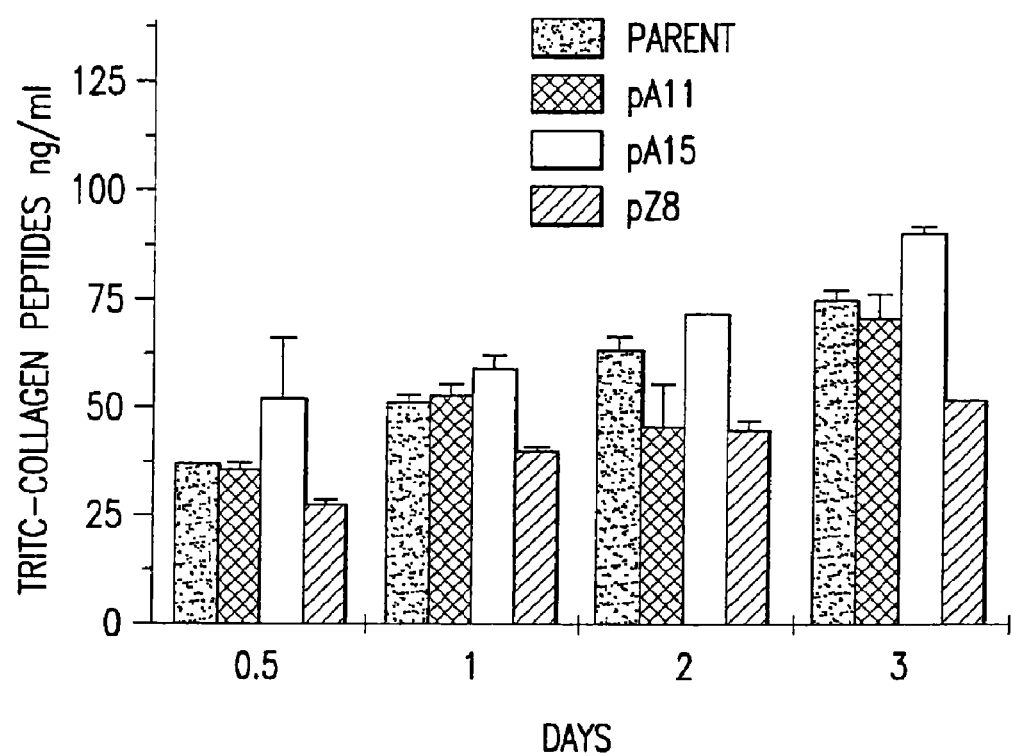
Figure 19B:
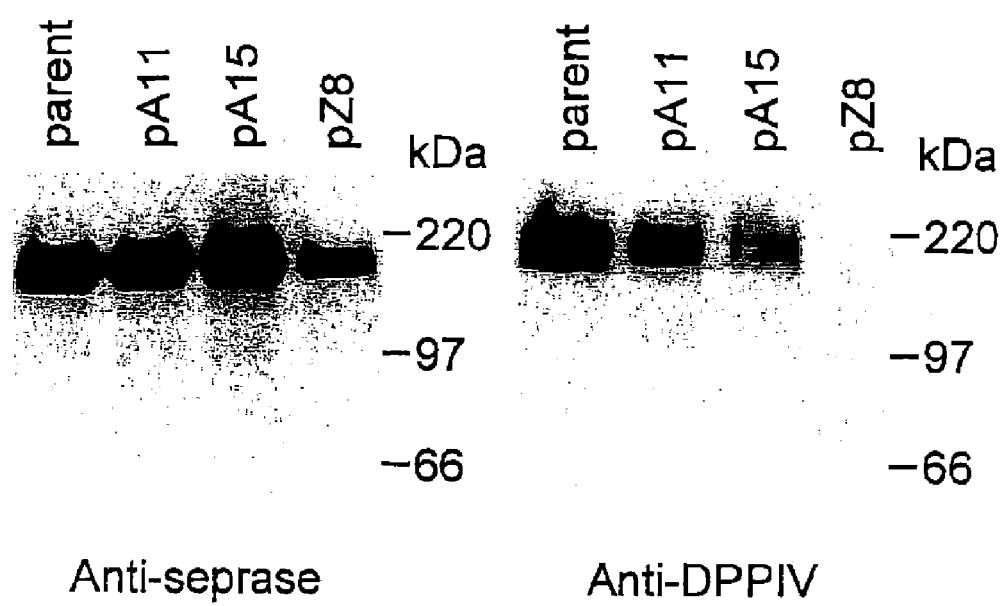

Cell transfection experiments were used to explore the cell surface association of seprase and DPPIV. MDA-MB-436 breast carcinoma cells that express constitutively the seprase-DPPIV complex were used. Cells over-expressing seprase or defective in DPPIV or seprase production were examined for their collagen-degrading and migratory activities in collagen gels (FIG. 19). An increase in release of TRITC-collagen peptides was observed in MDA-MB-436 cells transfected with plasmid pA15 that encodes seprase (FIG. 19A, pA15) and a decrease of peptide release was seen in cells transfected with a construct that encodes a DPPIV specific ribozyme (FIG. 19A, pZ8) as compared to parental or vector transfected cells (FIG. 19A; Parent, pA11). Also, over-expression of seprase appears to associate with a slight reduction of DPPIV, and cells transfected with the DPPIV ribozyme produce no detectable DPPIV and substantially reduced seprase (FIG. 19B).

The present invention is not to be limited in scope by the specific embodiments described herein, which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims. Various publications are cited herein that are hereby incorporated by reference in their entireties.

The invention claimed is:

1. A capture system for removing cancer cells from a blood fluid containing a mixed population of cancer cells and non-cancer cells, said fluid selected from the group consisting of whole blood, lymph, bone marrow, ascites or a combination thereof, said system comprising a vessel, said vessel comprising a cell-adhesion matrix having a fibrous scaffold coated with at least one adhesion molecule, said fibrous scaffold comprising type I collagen fibers, type III collagen fibers, fibrin, cotton fibers, tissue fragment or plastic fibers,
  wherein said cancer cells are isolated by incubating the mixed population of cells for a time sufficient to allow said cancer cells to ingest the matrix and isolating said cancer cells that ingest the matrix from cells that do not ingest the matrix.

2. The system of claim 1, further comprising an enzyme for releasing said cancer cells that have ingested the matrix.

3. The system of claim 2, wherein said enzyme comprises collagenase and proteases digesting cell-adhesion matrix.

4. The system of claim 2, wherein said enzyme comprises collagenase and trypsin.

5. The system of claim 1, wherein said system has a level of sensitivity of one viable cancer cell per ml of blood fluid.

6. The system of claim 1, wherein the matrix is labeled with a fluorescent label.

7. The system of claim 1, wherein the matrix is labeled with a radioactive label.

8. The system of claim 1, wherein the matrix is labeled with a color label.

9. The system of claim 1, wherein the matrix is labeled with a cytotoxic compound.

10. The system of claim 1, wherein the at least one adhesion molecule comprises fibronectin.

11. The system of claim 1, wherein the at least one adhesion molecule comprises laminin.

12. The system of claim 1, wherein the at least one adhesion molecule comprises vitronectin.

13. The system of claim 1, further comprising an anticoagulant to prevent said blood fluid from coagulating when said blood fluid is contacted with said matrix.

14. The system of claim 13, wherein said anticoagulant comprises heparin.

15. The system of claim 13, wherein said anticoagulant comprises citrate dextrose.

16. A capture system for removing cancer cells from a blood fluid containing a mixed population of cancer cells and non-cancer cells, said fluid selected from the group consisting of whole blood, lymph, bone marrow, ascites or a combination thereof, said system comprising:
  (i) a vessel comprising a cell-adhesion matrix having a fibrous scaffold coated with at least one adhesion molecule, said fibrous scaffold comprising type I collagen fibers, type III collagen fibers, fibrin, cotton fibers, tissue fragment or plastic fibers, wherein said cancer cells are isolated by incubating the mixed population of cells for a time sufficient to allow said cancer cells to ingest the matrix and isolating said cancer cells that ingest the matrix from cells that do not ingest the matrix; and (ii) an enzyme for releasing said cancer cells that have ingested the matrix.

17. The system of claim 16, further comprising an anticoagulant to prevent said blood fluid from coagulating when said blood fluid is contacted with said matrix.

18. A capture system for removing cancer cells from a blood fluid containing a mixed population of cancer cells and non-cancer cells, said fluid selected from the group consisting of whole blood, lymph, bone marrow, ascites or a combination thereof, said system comprising:

(i) a vessel comprising a cell-adhesion matrix having a fibrous scaffold coated with at least one adhesion molecule, said fibrous scaffold comprising type I collagen fibers, type III collagen fibers, fibrin, cotton fibers, tissue fragment or plastic fibers, wherein said cancer cells are isolated by incubating the mixed population of cells for a time sufficient to allow said cancer cells to ingest the matrix and isolating said cancer cells that ingest the matrix from cells that do not ingest the matrix;

(ii) an enzyme for releasing said cancer cells that have ingested the matrix; and (iii) an anticoagulant to prevent said blood fluid from coagulating when said blood fluid is contacted with said matrix.

* * * * *

UNITED STATES PATENT AND TRADEMARK OFFICE
CERTIFICATE OF CORRECTION

PATENT NO. : 8,288,116 B2
APPLICATION NO. : 12/725036
DATED : October 16, 2012
INVENTOR(S) : Wen-Tien Chen It is certified that error appears in the above-identified patent and that said Letters Patent is hereby corrected as shown below:

In the Specifications:

Column 37, line 2

Now reads: "These indicate that integrins may be primary"

Should read: -- These indicate that β1 integrins may be primary --

Signed and Sealed this
Twenty-first Day of May, 2013

Teresa Stanek Rea
*Acting Director of the United States Patent and Trademark Office*